US009272246B2

(12) United States Patent
Rasmussen et al.

(10) Patent No.: US 9,272,246 B2
(45) Date of Patent: *Mar. 1, 2016

(54) LIGAND FUNCTIONAL SUBSTRATES

(75) Inventors: Jerald K. Rasmussen, Woodville, WI (US); Catherine A. Bothof, Stillwater, MN (US); Kannan Seshadri, Woodbury, MN (US); James I. Hembre, Plymouth, MN (US); Robert T. Fitzsimons, Jr., Minneapolis, MN (US); George W. Griesgraber, Eagan, MN (US); Yi He, Roseville, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 609 days.

This patent is subject to a terminal disclaimer.

(21) Appl. No.: 13/353,413

(22) Filed: Jan. 19, 2012

(65) Prior Publication Data

US 2012/0252091 A1    Oct. 4, 2012

Related U.S. Application Data

(60) Provisional application No. 61/468,302, filed on Mar. 28, 2011.

(51) Int. Cl.
*C12N 9/00* (2006.01)
*B01D 67/00* (2006.01)
*B01D 71/56* (2006.01)
*C09D 179/02* (2006.01)

(52) U.S. Cl.
CPC ............ *B01D 67/0093* (2013.01); *B01D 71/56* (2013.01); *C09D 179/02* (2013.01); *B01D 2323/30* (2013.01); *B01D 2323/385* (2013.01); *Y10T 428/31663* (2015.04); *Y10T 428/31721* (2015.04); *Y10T 428/31725* (2015.04); *Y10T 428/31855* (2015.04); *Y10T 428/31928* (2015.04)

(58) Field of Classification Search
CPC ........................................................ C12N 9/00
USPC ....................................................... 435/183
See application file for complete search history.

(56) References Cited

U.S. PATENT DOCUMENTS

| 3,018,262 | A | 1/1962 | Schroeder |
| 3,298,998 | A | 1/1967 | McConnell |
| 3,876,738 | A | 4/1975 | Marinacchio |
| 3,928,517 | A | 12/1975 | Knight |
| 4,157,418 | A | 6/1979 | Heilmann |
| 4,529,256 | A | 7/1985 | Kretzschmar |
| 4,707,265 | A | 11/1987 | Barnes, Jr. |
| 4,726,989 | A | 2/1988 | Mrozinski |
| 4,867,881 | A | 9/1989 | Kinzer |
| 5,120,594 | A | 6/1992 | Mrozinski |
| 5,260,360 | A | 11/1993 | Mrozinski |
| 5,458,782 | A | 10/1995 | Hou |
| 5,506,279 | A | 4/1996 | Babu |
| 5,912,306 | A | 6/1999 | Pudney |
| 5,962,544 | A | 10/1999 | Waller, Jr. |
| 6,056,529 | A | 5/2000 | Meyering |
| 6,150,103 | A | 11/2000 | Ness |
| 6,267,916 | B1 | 7/2001 | Meyering |
| 6,413,070 | B1 | 7/2002 | Meyering |
| 6,514,660 | B1 | 2/2003 | Majumdar |
| 6,776,940 | B2 | 8/2004 | Meyering |
| 6,780,327 | B1 | 8/2004 | Wu |
| 6,893,685 | B2 | 5/2005 | Qiu |
| 7,125,603 | B2 | 10/2006 | David |
| 7,338,692 | B2 | 3/2008 | Smith |
| 7,556,858 | B2 | 7/2009 | Rasmussen |
| 8,846,203 | B2 * | 9/2014 | Bothof et al. ................. 428/500 |
| 2008/0014625 | A1 | 1/2008 | Etzel |
| 2010/0075131 | A1 | 3/2010 | Seshadri |
| 2010/0075560 | A1 | 3/2010 | Seshadri |
| 2011/0033633 | A1 | 2/2011 | Bothof |
| 2011/0184078 | A1 | 7/2011 | Etzel |
| 2011/0201078 | A1 | 8/2011 | Rasmussen |
| 2011/0217752 | A1 * | 9/2011 | Rasmussen et al. .......... 435/183 |

FOREIGN PATENT DOCUMENTS

| WO | WO 96/37241 | 11/1996 |
| WO | WO 2009/146321 | 12/2009 |
| WO | WO 2009/148869 | 12/2009 |
| WO | WO 2011/109151 | 9/2011 |

OTHER PUBLICATIONS

PCT International Search Report, PCT/US2012/024310, dated May 21, 2012.*
Rasmussen, et al., "Polyazlactones," Encyclopedia of Polymer Science and Engineering, Second Edition, vol. 11, pp. 558-571, 1988.
Bialk, et al., "Grafting of polymers to solid surfaces by using immobilized methacrylates," Colloids and Surfaces A: Physicochemical and Engineering Aspects, vol. 198-200, pp. 543-549.
Wente et al., "Manufacture of Superfine Organic Fibers," Navel Research Laboratories Report No. 4364, 1954.
Wente, "Superfine Thermoplastic Fibers," Industrial and Engineering Chemistry, Naval Research Laboratory, vol. 48, No. 8, pp. 1342-1346, 1956.
Towns, et al., "Polyethyleneimine-bonded phases in the separation of proteins by capillary electrophoresis," Journal of Chromatography, vol. 516, pp. 59-78, 1990.
Laible, et al., "Formation of Chemically Bound Polymer Layers on Oxide Surfaces and Their Role in Colloidal Stability," Advances in Colloid and Interface Science, vol. 13, pp. 65-99, 1980.

* cited by examiner

*Primary Examiner* — Scarlett Goon
*Assistant Examiner* — Sonya Wright
(74) *Attorney, Agent, or Firm* — Kent S. Kokko

(57) ABSTRACT

A substrate comprising a crosslinked polymer primer layer, and grafted thereto a ligand-functionalized polymer is provided. The grafted polymer has the requisite affinity for binding neutral or negatively charged biomaterials, such as cells, cell debris, bacteria, spores, viruses, nucleic acids, and proteins, at pH's near or below the pI's of the biomaterials.

18 Claims, No Drawings

LIGAND FUNCTIONAL SUBSTRATES

CROSS REFERENCE TO RELATED APPLICATION

This application claims the benefit of U.S. Provisional Patent Application No. 61/468,302, filed Mar. 28, 2011, the disclosure of which is incorporated by reference herein in its entirety.

TECHNICAL FIELD

The present disclosure relates to ligand-functionalized substrates, and methods for preparing the same. The functionalized substrates are useful in selectively binding and removing biological materials, such as viruses, from biological samples.

BACKGROUND

Detection, quantification, isolation and purification of target biomaterials, such as viruses and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules are important for therapeutic uses and in biomedical research. Biomacromolecules such as enzymes which are a special class of proteins capable of catalyzing chemical reactions are also useful industrially; enzymes have been isolated, purified, and then utilized for the production of sweeteners, antibiotics, and a variety of organic compounds such as ethanol, acetic acid, lysine, aspartic acid, and biologically useful products such as antibodies and steroids.

In their native state in vivo, structures and corresponding biological activities of these biomacromolecules are maintained generally within fairly narrow ranges of pH and ionic strength. Consequently, any separation and purification operation must take such factors into account in order for the resultant, processed biomacromolecule to have potency.

The use of certain ionic polymers, especially cationic polymers, for the flocculation of cell and/or cell debris, as well as for the precipitation of proteins, is known. Similarly, ionic polymers have been used to modify filtration media to enhance the removal of impurities from process streams in depth filtration or membrane adsorber type applications. The effectiveness of these polymers is typically reduced as the conductivity of the media being processed increases, i.e. as the salt content increases. There is a need in the art for polymeric materials with increased affinity for biological species under high ionic strength conditions.

Chromatographic separation and purification operations can be performed on biological product mixtures, based on the interchange of a solute between a moving phase, which can be a gas or liquid, and a stationary phase. Separation of various solutes of the solution mixture is accomplished because of varying binding interactions of each solute with the stationary phase; stronger binding interactions generally result in longer retention times when subjected to the dissociation or displacement effects of a mobile phase compared to solutes which interact less strongly and, in this fashion, separation and purification can be effected.

Most current capture or purification chromatography is done via conventional column techniques. These techniques have severe bottlenecking issues in downstream purification, as the throughput using this technology is low. Attempts to alleviate these issues include increasing the diameter of the chromatography column, but this in turn creates challenges due to difficulties of packing the columns effectively and reproducibly. Larger column diameters also increase the occurrence of problematic channeling. Also, in a conventional chromatographic column, the adsorption operation is shut down when a breakthrough of the desired product above a specific level is detected. This causes the dynamic or effective capacity of the adsorption media to be significantly less than the overall or static capacity. This reduction in effectiveness has severe economic consequences, given the high cost of some chromatographic resins.

Polymeric resins are widely used for the separation and purification of various target compounds. For example, polymeric resins can be used to purify or separate a target compound based on the presence of an ionic group, based on the size of the target compound, based on a hydrophobic interaction, based on an affinity interaction, or based on the formation of a covalent bond. There is a need in the art for polymeric substrates having enhanced affinity for viruses and other biological species to allow selective removal from a biological sample. There is further need in the art for ligand functionalized membranes that overcome limitations in diffusion and binding, and that may be operated at high throughput and at lower pressure drops.

SUMMARY OF THE INVENTION

The present disclosure is directed to ligand-functionalized polymers, methods of making the same, and substrates bearing a grafted coating of the ligand-functional polymers. More specifically, the substrate comprises a crosslinked polymer primer layer, and grafted thereto a ligand-functionalized polymer. The grafted polymer has the requisite affinity for binding neutral or negatively charged biomaterials, such as cells, cell debris, bacteria, spores, viruses, nucleic acids, and proteins, at pH's near or below the pI's of the biomaterials.

"Alkyl" means a linear or branched, cyclic or acyclic, saturated monovalent hydrocarbon having from one to about twelve carbon atoms, e.g., methyl, ethyl, 1-propyl, 2-propyl, pentyl, and the like.

"Alkylene" means a linear saturated divalent hydrocarbon having from one to about twelve carbon atoms or a branched saturated divalent hydrocarbon having from three to about twelve carbon atoms, e.g., methylene, ethylene, propylene, 2-methylpropylene, pentylene, hexylene, and the like.

"Alkenyl" means a linear unsaturated monovalent hydrocarbon having from two to about twelve carbon atoms or a branched unsaturated hydrocarbon having from three to about twelve carbon atoms.

"Aryl" means a monovalent aromatic, such as phenyl, naphthyl and the like.

"Arylene" means a polyvalent, aromatic, such as phenylene, naphthalene, and the like.

"Aralkylene" means a group defined above with an aryl group attached to the alkylene, e.g., benzyl, 1-naphthylethyl, and the like.

"Heteroarylene" refers to a divalent group that is aromatic and heterocyclic. That is, the heteroarylene includes at least one heteroatom in an aromatic ring having 5 or 6 members. Suitable heteroatoms are typically oxy, thio, or amino. The group can have one to five rings that are connected, fused, or a combination thereof. At least one ring is heteroaromatic and any other ring can be aromatic, non-aromatic, heterocyclic, carbocyclic, or a combination thereof. In some embodiments, the heteroarylene has up to 5 rings, up to 4 rings, up to 3 rings, up to 2 rings, or one ring. Examples of heteroarylene groups include, but are not limited to, triazine-diyl, pyridine-diyl, pyrimidine-diyl, pyridazine-diyl, and the like.

"hydrocarbyl" is inclusive of aryl and alkyl;

"(Hetero)hydrocarbyl" is inclusive of hydrocarbyl alkyl and aryl groups, and heterohydrocarbyl heteroalkyl and heteroaryl groups, the later comprising one or more catenary (in-chain) heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

"(Hetero)arylene" is inclusive of arylene and heteroarylene.

DETAILED DESCRIPTION OF THE INVENTION

In the article and methods of this invention, ligand-functionalized substrates are provided which have enhanced affinity and/or capacity, especially in high ionic strength media, for biological materials, such as host cell proteins, DNA, RNA, viruses, and other microorganisms, at pH's near or below the pI's of the biological materials. The affinity for such biomaterials allows materials that are positively charged at those pH's, such as antibodies, to be purified, as they are not bound to the ligand functional groups. The ligand functionalized substrate allows the selective capture or binding of target biomaterials by the ligand groups, while other materials, lacking the affinity for the ligand groups, are passed.

The ligand functional substrate comprises a) a substrate; b) a primer layer disposed on the substrate comprising the reaction product of: 1) a polyamine polymer, 2) a polyfunctional crosslinking agent for the polyamine polymer, and 3) an amine reactive monomer having a polymerizable, ethylenically unsaturated group, preferably a (meth)acryloyl group, and an amine-reactive functional group; and c) a ligand-functional alkenyl (co)polymer layer grafted to the primer layer. The primer layer is coated on the substrate and cured to form a durable, crosslinked polyamine polymer layer having polymerizable, ethylenically unsaturated groups, preferably (meth)acryloyl groups, on the surface thereof. The crosslinking of the polyamine polymer is effected by the 2) polyfunctional crosslinking agent, which has two or more amine-reactive functional groups, such as epoxy groups. The crosslinked polyamine polymer is simultaneously or sequentially functionalized with primer component 3), having an amine-reactive group for coupling (by forming a covalent bond) to the crosslinked polyamine polymer, and an ethylenically unsaturated group, such as a (meth)acryloyl group, which may be used to free-radically graft the c) ligand-functional alkenyl (co)polymer layer to the crosslinked polyamine polymer layer.

Polyamine Polymer

The primer base polymer comprises a polyamine polymer; i.e. a polymer having primary or secondary amino groups that may be pendent or catenary, i.e. in the polymer chain. The aminopolymers contain primary or secondary amine groups and can be prepared by chain growth or step growth polymerization procedures with the corresponding monomers. These monomers can also, if desired, be copolymerized with other monomers. The polymer can also be a synthesized or naturally occurring biopolymer. If any of these polymers, irrespective of source, do not contain primary or secondary amine groups, these functional groups can be added by the appropriate chemistry.

Useful aminopolymers are water soluble or water-dispersible. As used herein, the term "water soluble" refers to a material that can be dissolved in water. The solubility is typically at least about 1 milligram, preferably 5 milligram, more preferably 10 milligram, per milliliter of water. As used herein, the term "water dispersible" refers to a material that is not water soluble but that can be emulsified or suspended in water. In some embodiments mixed aqueous/alcoholic solvent systems may be advantageous.

Examples of aminopolymers suitable for use, which are prepared by chain growth polymerization include, but are not limited to: polyvinylamine, poly(N-methylvinylamine), polyethylenimine, polypropylenimine, polyallylamine, polyallylmethylamine, polydiallylamine, poly(-aminomethylstyrene), poly(4-aminostyrene), poly(acrylamide-co-methylaminopropylacrylamide), and poly(acrylamide-co-aminoethylmethacrylate).

Examples of amino polymers suitable for use, which are prepared by step growth polymerization include, but are not limited to: polyethylenimine, polypropylenimine, polylysine, polyornithine, polyaminoamides, polydimethylamine-epichlorohydrin-ethylenediamine, and certain polyaminosiloxanes, which can be built from monomers such as aminopropyltriethoxysilane, N-(2-aminoethyl)-3-aminopropyltrimethoxysilane, N-trimethoxysilylpropyl-N-methylamine, and bis(trimethoxysilylpropyl)amine.

Useful aminopolymers may also include those that have primary or secondary amino end groups and include, but are not limited to, those formed from polyamidoamine (PAMAM) and polypropylenimine: e.g. DAB-Am and PAMAM dendrimers (or hyperbranched polymers containing the amine functional group). Dendrimeric material formed from PAMAM are commercially available under the trade designation Starburst™ (PAMAM) dendrimer (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical, Milwaukee, Wis. Dendrimeric material formed from polypropylenimine is commercially available under the trade designation "DAB-AM" from Aldrich Chemical. For example, DAB-Am-4 is a generation 1 polypropylenimine tetraamine dendrimer with 4 primary amino groups, DAB-Am-8 is a generation 2 polypropylenimine octaamine dendrimer with 8 primary amino groups, DAB-Am-16 is a generation 3 polypropylenimine hexadecaamine with 16 primary amino groups, DAB-Am-32 is a generation 4 polypropylenimine dotriacontaamine dendrimer with 32 primary amino groups, and DAB-Am-64 is a generation 5 polypropylenimine tetrahexacontaamine dendrimer with 64 primary amino groups.

Examples of aminopolymers suitable for use, which are biopolymers include chitosan, glucosamine- and galactosamine-containing polysaccharides, and starch, where the latter is reacted with reagents such as methylaminoethylchloride.

Other categories of aminopolymers suitable for use include polyacrylamide homo- or copolymers with amino monomers including aminoalkyl(meth)acrylate, (meth)acrylamidoalkylamine, and diallylamine.

Preferred aminopolymers include polyamidoamines, polyethyleneimine, polyvinylamine, polyallylamine, and polydiallylamine.

Suitable commercially available aminopolymers include, but are not limited to, polyamidoamines such as ANQUAMINE™ 360, 401, 419, 456, and 701 (Air Products and Chemicals, Allentown, Pa.); LUPASOL™ polyethylenimine polymers such as FG, PR 8515, Waterfree, P, PS (BASF Corporation, Rensselaer, N.Y.); polyethylenimine polymers such as CORCAT™ P-600 (EIT Company, Lake Wylie, S.C.); and polyamide resins such as the VERSAMID series of resins that are formed by reacting a dimerized unsaturated fatty acid with polyalkylene polyamines (Cognis Corporation, Cincinnati, Ohio).

The primer layer has a crosslinking agent for the polyamine polymer having at least two amine-reactive functional groups, including ketone, aldehyde, ester, acyl halide, isocyanate, epoxide, anhydride, or azlactone groups. Preferably the amine-reactive functional groups Z are selected to react with the amine groups of the polyamine polymer at temperatures below about 50° C., preferably below 25° C. such that the crosslinking reaction takes place during the coating and drying operation. Preferable crosslinking agents are further water-soluble or water-dispersible.

Such crosslinking agents may have the general formula 1:

$$R^8 \text{—} (Z)_y, \quad 1$$

where $R^8$ is a (hetero)hydrocarbyl group, Z is an amine-reactive group and y is ≥2, preferably 2-4. The $R^8$ group may be an alkylene group, an arylene group, a heteroarylene group, a heteroalkylene group, an aralkylene group, or a combination thereof.

In one embodiment the amine-reactive Z group may be an epoxy group and include both aliphatic and aromatic polyepoxides. Representative examples of aliphatic polyepoxides include 3',4'-epoxycyclohexylmethyl-3,4-epoxycyclohexanecarboxylate, 3,4-epoxycyclohexyloxirane, 2-(3',4'-epoxycyclohexyl)-5,1"-spiro-3",4"-epoxycyclohexane-1,3-dioxane, bis(3,4-epoxycyclohexylmethyl)adipate, the diglycidyl ester of linoleic dimer acid, 1,4-bis(2,3-epoxypropoxy)butane, 4-(1,2-epoxyethyl)-1,2-epoxycyclohexane, 2,2-bis(3,4-epoxycyclohexyl)propane, polyglycidyl ethers of aliphatic polyols such as glycerol, ethylene glycol, polyethylene glycol or butanediol. Representative examples of aromatic polyepoxides which can be utilized in the composition of the invention include glycidyl esters of aromatic carboxylic acids, e.g., phthalic acid diglycidyl ester, isophthalic acid diglycidyl ester, trimellitic acid triglycidyl ester, and pyromellitic acid tetraglycidyl ester, and mixtures thereof; N-glycidylaminobenzenes, e.g., N,N-diglycidylbenzeneamine, bis(N,N-diglycidyl-4-aminophenyl)methane, 1,3-bis(N,N-diglycidylamino)benzene, and N,N-diglycidyl-4-glycidyloxybenzeneamine, and mixtures thereof; and the polyglycidyl derivatives of polyhydric phenols, e.g., 2,2-bis-[4-(2,3-epoxypropoxy)phenyl]propane, the polyglycidyl ethers of polyhydric phenols such as tetrakis(4-hydroxyphenyl)ethane, pyrocatechol, resorcinol, hydroquinone, 4,4'-dihydroxydiphenyl methane, 4,4' dihydroxydiphenyl dimethyl methane, 4,4'-dihydroxy-3,3'-dimethyldiphenyl methane, 4,4'-dihydroxydiphenyl methyl methane, 4,4'-dihydroxydiphenyl cyclohexane, 4,4'-dihydroxy-3,3'-dimethyldiphenyl propane, 4,4'-dihydroxydiphenyl sulfone, and tris-(4-hydroxyphenyl)methane, polyglycidyl ethers of novolacs (reaction products of monohydric or polyhydric phenols with aldehydes in the presence of acid catalysts), and the derivatives described in U.S. Pat. Nos. 3,018,262 and 3,298,998, the descriptions of which are incorporated herein by reference, as well as the derivatives described in the Handbook of Epoxy Resins by Lee and Neville, McGraw-Hill Book Co., New York (1967), and mixtures thereof.

In one embodiment the amine reactive functional group Z may be an isocyanate group. Suitable polyisocyanates include organic compounds containing at least two free isocyanate groups. Diisocyanates of the formula $R^8(NCO)_2$ are preferably used wherein $R^8$ denotes an aliphatic hydrocarbon group with 4 to 20 carbon atoms, a cycloaliphatic hydrocarbon group with 6 to 20 carbon atoms, an aromatic hydrocarbon group with 6 to 20 carbon atoms or an araliphatic hydrocarbon group with 7 to 20 carbon atoms.

Examples of diisocyanates include tetramethylene diisocyanate, hexamethylenediisocyanate (HDI), dodecamethylenediisocyanate, 1,4-diisocyanatocy clohexane, 1-isocyanato-3,3,5-trimethyl-5-isocyanatomethylcyclohexane (IPDI), 4,4' diisocyanato-dicyclohexylmethane (HMDI), 4,4'-diisocyanato-2,2-dicyclohexyl-propane, 1,4-diisocyanatobenzene, 2,4-diisocyanatotoluene (TDI), 2,6 diisocyanatotoluene, 4,4'-diisocyanatodiphenylmethane (MDI), m- and p xylylenediisocyanate, α,α,α',α'-tetramethyl-m- and p-xylylenediisocyanate and mixtures of these compounds. Suitable polyisocyanates also include triisocyanates such as 1,3,5 triisocyanatocyclohexane-s-trione, isocyanurate and biuret derivatives of HDI and MDI.

In one embodiment the amine reactive functional group Z may be an azlactone group. Reference may be made to Table 1 of a review entitled "Polyazlactones" by J. K. Rasmussen, et al., Encyclopedia of Polymer Science and Engineering, Second Edition, Volume 11, 1988, pp. 558-571 that contains a listing of reported bis(azlactones). Other poly azlactone functional materials are described in U.S. Pat. No. 7,556,858 (Rasmussen et al.), incorporated herein by reference.

In one embodiment the amine reactive functional group Z may be an aldehyde or ketone group. Examples include bis- and polyaldehydes, such as glyoxal or glutaraldehyde.

In some embodiments the crosslinking agent may be a polyacyl compound where Z is an ester, acid, acid halide or anhydride group. Esters and acids are less preferred due to the reduced reactivity. Representative examples of suitable diacyl compounds, as the corresponding esters, halides, acids, and anhydrides: azelaic; maleic; fumaric; itaconic; 1,5-pent-2-enedioic; adipic; 2-methyleneadipic; 3-methylitaconic; 3,3-dimethylitaconic; sebacic; suberic; pimelic; succinic; benzylsuccinic; sulfosuccinic; glutaric; 2-methyleneglutaric; 2-sulfoglutaric; 3-sulfoglutaric; diglycolic; dilactic; 3,3'-(ethylenedioxy)dipropionic; dodecanedioic; 2-sulfododecanedioic; decanedioic; undecanedicarboxylic; hexadecanedicarboxylic; dimerized fatty acids (such as those obtained by the dimerization of olefinically unsaturated monocarboxylic acids containing 16 to 20 carbon atoms, for example, oleic acid and linoleic acid and the like); 1,2-, 1,4-, and 1,6-cyclohexanedicarboxylic; norbornenedicarboxylic; bi-cyclooctanedicarboxylic; and other aliphatic, heteroaliphatic, saturated alicyclic, or saturated heteroalicyclic dicarboxylic acids; and the like; and mixtures thereof. Salts (for example, alkali metal salts) of the above-described sulfonic acids can also be used.

The crosslinking agent for the polyamine polymer may be provided in an amount wherein the number of equivalents of amine reactive groups Z is at least 2%, preferably at least 5%, and up to about 20%, relative to the number of equivalents of amine groups in the polyamine polymer.

The primer layer further comprises an amine reactive monomer having a polymerizable, ethylenically unsaturated group and an amine-reactive functional group, some embodiments of which are of the formula 2:

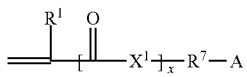

wherein $X^1$ is —O— or —NR$^1$—, where R$^1$ is H or C$_1$-C$_4$ alkyl,

R$^1$ is H or C$_1$-C$_4$ alkyl;

R$^7$ is a single bond or a (hetero)hydrocarbyl linking group,

A is a functional group that is reactive with the amino groups of the polyamine polymer, and x is 0 or 1.

In some embodiments compounds of Formula 2 are (meth)acryloyl compounds, and in other embodiments are alkenyl compounds.

Preferably, R$^7$ is a single bond or a hydrocarbyl linking group that joins an ethylenically unsaturated, polymerizable group (e.g. alkenyl or (meth)acryl group) to reactive functional group A and preferably is an alkylene group having 1 to 6 carbon atoms, a 5- or 6-membered cycloalkylene group having 5 to 10 carbon atoms, or a divalent aromatic group having 6 to 16 carbon atoms; and A is a reactive functional group capable of reacting with an amine group of the polyamine polymer for the incorporation of a free-radically polymerizable group.

Useful reactive functional groups "A" include carboxyl, oxazolinyl, azlactone, acetyl, acetonyl, acetoacetyl, ester, isocyanato, epoxy, aziridinyl, acyl halide, and cyclic anhydride groups. Preferably the amine-reactive functional groups A are selected to react with the amine groups of the polyamine polymer at temperatures below about 50° C., preferably below 25° C. such that the reaction takes place during the coating and drying operation. Preferable amine reactive monomers are further water-soluble or water-dispersible.

Representative azlactone group-substituted functional compounds of Formula 2 include: 2-ethenyl-1,3-oxazolin-5-one; 2-ethenyl-4-methyl-1,3-oxazolin-5-one; 2-isopropenyl-1,3-oxazolin-5-one; 2-isopropenyl-4-methyl-1,3-oxazolin-5-one; 2-ethenyl-4,4-dimethyl-1,3-oxazolin-5-one; 2-isopropenyl-4,4-dimethyl-1,3-oxazolin-5-one; 2-ethenyl-4-methyl-4-ethyl-1,3-oxazolin-5-one; 2-isopropenyl-3-oxa-1-aza[4.5]spirodec-1-ene-4-one; 2-ethenyl-5,6-dihydro-4H-1,3-oxazin-6-one; 2-ethenyl-4,5,6,7-tetrahydro-1,3-oxazepin-7-one; 2-isopropenyl-5,6-dihydro-5,5-di(2-methylphenyl)-4H-1,3-oxazin-6-one; 2-acryloyloxy-1,3-oxazolin-5-one; 2-(2-acryloyloxy)ethyl-4,4-dimethyl-1,3-oxazolin-5-one; 2-ethenyl-4,5-dihydro-6H-1,3-oxazin-6-one; and 2-ethenyl-4,5-dihydro-4,4-dimethyl-6H-1,3-oxazin-6-one.

Representative acetoacetyl group-substituted functional compounds of Formula 2 include 2-(acetoacetoxy)ethyl methacrylate.

Representative carboxyl group-substituted functional compounds of Formula 2 include (meth)acrylic acid, 3-(meth)acryloyloxy-propionic acid, 4-(meth)acryloyloxy-butyric acid, 2-(meth)acryloyloxy-benzoic acid, 3-(meth)acryloyloxy-5-methyl benzoic acid, 4-(meth)acryloyloxymethyl-benzoic acid, phthalic acid mono-[2-(meth)acryloyloxy-ethyl]ester, 2-butynoic acid, and 4-pentynoic acid.

Representative isocyanate group-substituted functional compounds of Formula 2 include 2-isocyanatoethyl (meth)acrylate, 3-isocyanatopropyl (meth)acrylate, 4-isocyanatocyclohexyl (meth)acrylate, 4-isocyanatostyrene, 2-methyl-2-propenoyl isocyanate, 4-(2-(meth)acryloyloxyethoxy-carbonylamino) phenylisocyanate, allyl 2-isocyanatoethyl-ether, and 3-isocyanato-1-propene.

Representative epoxy group-substituted functional compounds of Formula 2 include glycidyl (meth)acrylate, thioglycidyl (meth)acrylate, 3-(2,3-epoxypropoxy)phenyl (meth)acrylate, 2-[4-(2,3-epoxypropoxy)phenyl]-2-(4-(meth)acryloyloxy-phenyl)propane, 4-(2,3-epoxypropoxy)cyclohexyl (meth)acrylate, 2,3-epoxycyclohexyl (meth)acrylate, and 3,4-epoxycyclohexyl (meth)acrylate.

Representative acyl halide group-substituted functional compounds of Formula 2 include (meth)acryloyl chloride, α-chloro(meth)acryloyl chloride, (meth)acryloyloxyacetyl chloride, 5-hexenoyl chloride, 2-(acryloyloxy) propionyl chloride, 3-(acryloylthioxy) propionoyl chloride, and 3-(N-acryloyl-N-methylamino) propionoyl chloride.

Other useful amine-reactive monomers include anhydride group-substituted functional monomers including maleic anhydride, (meth)acrylic anhydride, itaconic anhydride, 3-(meth)acryloyloxyphthalic anhydride, and 2-(meth)acryloxycyclohexanedicarboxylic acid anhydride.

Ligand Monomer

Grafted to the primer layer is a ligand-functional alkenyl, preferably a (meth)acryloyl, (co)polymer layer. More specifically, the ligand-functional (meth)acryloyl (co)polymer layer is grafted to the pendent ethylenically unsaturated, polymerizable groups derived from the amine reactive monomer (such as those of Formula 2), which in turn is covalently attached to the polyamine polymer by means of the reaction between the amine groups of the polyamine and the amine reactive functional group "A".

The ligand-functional (meth)acryloyl (co)polymer comprises polymerized monomer units of the formula 3:

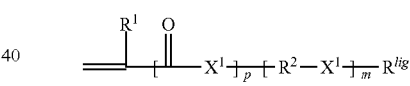

where

R$^1$ is H or C$_1$-C$_4$ alkyl;

R$^2$ is a (hetero)hydrocarbyl group, preferably a divalent alkylene having 1 to 20 carbon atoms;

X$^1$ is —O— or —NR$^3$—, where R$^3$ is independently H or hydrocarbyl preferably C$_1$-C$_4$ alkyl;

R$^{lig}$ is a ligand-containing group, p is 0 or 1; and m is 0 or 1.

The R$^{lig}$ group may contain any functional group that will selectively bind a biomacromolecule of interest, and may be selected from traditional ligands such as primary, secondary, tertiary, or quaternary amine containing ligands; multifunctional ligands such as tyrosinol, tryptophanol, octopamine, 2-aminobenzimidazole, 1,3-diamino-2-hydroxypropane, tris (2-aminoethyl)amine, diethylenetriamine, triethylenetetramine, tetraethylenepentamine, or agmatine containing ligands; and guanidine and biguanide group containing ligands In some embodiments, the ligand-functional alkenyl (co)polymer comprises polymerized ligand-functional monomer units of the formula 4a or b:

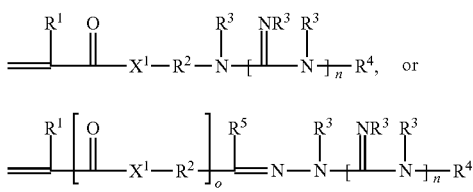

wherein
$R^1$ is H or $C_1$-$C_4$ alkyl;
$R^2$ is a (hetero)hydrocarbyl group, preferably a divalent alkylene having 1 to 20 carbon atoms;
each $R^3$ is independently H or hydrocarbyl, preferably $C_1$-$C_4$ alkyl;
$R^4$ is H, $C_1$-$C_4$ alkyl or —$N(R^3)_2$;
$R^5$ is H or hydrocarbyl, preferably $C_1$-$C_4$ alkyl or aryl;
$X^1$ is —O— or —$NR^3$—,
o is 0 or 1, and
n is 1 or 2.

Such ligand monomers may be made by condensation of an alkenyl or alkenoyl compound, typically a (meth)acryloyl halide, a (meth)acryloylisocyanate, or an alkenylazlactone, with a compound of formulas 5a or 5b:

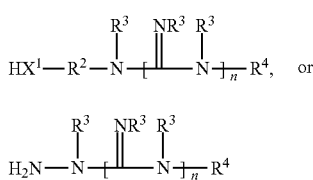

where $X^1$, and $R^2$ to $R^4$, and n are as previously defined.

Other ligand monomers may be made by condensation of a carbonyl containing monomer, such as acrolein, vinylmethylketone, diacetone acrylamide or acetoacetoxyethylmethacrylate, with a compound of formulas 5a or 5b.

Preferably, the ligand-functional alkenyl (co)polymer layer also comprises units derived from a (meth)acryloyl monomer containing at least two free radically polymerizable groups. Such multifunctional (meth)acryloyl monomer, including (meth)acrylate and (meth)acrylamide monomers may be incorporated into the blend of polymerizable monomers to assist in branching or lightly crosslinking of the grafted ligand-functional copolymer. Examples of useful multifunctional (meth)acrylates include, but are not limited to, di(meth)acrylates, tri(meth)acrylates, and tetra(meth)acrylates, such as ethyleneglycol di(meth)acrylate, 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, methylenebisacrylamide, ethylenebisacrylamide, hexamethylenebisacrylamide, diacryloylpiperazine, and mixtures thereof.

Surprisingly, it has been found that inclusion of such a multifunctional (meth)acrylate or (meth)acrylamide monomer typically increases the capacity, particularly the dynamic binding capacity, of the grafted article for capturing biological species. Such comonomers are used in amounts of about 0.25% to about 5% by weight, preferably of about 1% to about 3% by weight, relative to the total monomer weight. Higher concentrations of polyfunctional comonomer often lead to decreased capacities. While not wanting to be bound by theory, it is believed that this comonomer promotes branching in the grafted (co)polymer layer, thereby leading to increased accessibility or availability of the ligand groups.

It has been observed that the incorporation of a multifunctional (meth)acrylate or (meth)acrylamide monomer enables the preparation of ligand functionalized articles without the use of the primer layer. However, the primer layer enables a broader formulation window within which one can maintain high functional capacity (static and dynamic binding capacity) of the resultant articles.

The ligand-functional alkenyl (co)polymer layer (grafted to the primer layer) may optionally comprise one or more hydrophilic monomers which comprise at least one alkenyl group, preferably a (meth)acryloyl group, and a hydrophilic group, including poly(oxyalkylene) and ionic groups, for providing hydrophilicity to the substrate, or for providing greater selectivity to the substrate when binding biomaterials.

The hydrophilic ionic groups may be neutral, have a positive charge, a negative charge, or a combination thereof. With some suitable ionic monomers, the ionic group can be neutral or charged depending on the pH conditions. This class of monomers is typically used to impart a desired hydrophilicity to the porous base substrate in addition to the c) monomer. In applications for viral capture, the addition of a grafting ionic monomer having a positive charge at the selected pH may allow selective binding of viruses while repelling positively charged biological materials such as antibodies.

In some preferred embodiments, the third monomer may have an acrylate group, or other ethylenically unsaturated groups of reduced reactivity, and a poly(alkylene oxide) group; e.g. monoacrylated poly(alkylene oxide compounds, where the terminus is a hydroxy group or an alkyl ether group.

In some embodiments the ionic monomers having a negative charge include (meth)acryloylsulfonic acids of Formula 6 or salts thereof

wherein, Y is a straight or branched alkylene (e.g., an alkylenes having 1 to 10 carbon atoms, 1 to 6 carbon atoms, or 1 to 4 carbon atoms) and L is —O— or —NR—, where $R^3$ is H or $C_1$-$C_4$ alkyl-; Exemplary ionic monomers according to Formula 6 include, but are not limited to, N-acrylamidomethanesulfonic acid, 2-acrylamidoethanesulfonic acid, 2-acrylamido-2-methyl-1-propanesulfonic acid, and 2-methacrylamido-2-methyl-1-propanesulfonic acid. Salts of these acidic monomers can also be used. Counter ions for the salts can be, for example, ammonium ions, potassium ions, lithium ions, or sodium ions.

Other suitable ionic grafting monomers having a negative charge (at a selected pH) include sulfonic acids such as vinylsulfonic acid and 4-styrenesulfonic acid; (meth)acrylamidophosphonic acids such as (meth)acrylamidoalkylphosphonic acids (e.g., 2-(meth)acrylamidoethylphosphonic acid and 3-(meth)acrylamidopropylphosphonic acid; acrylic acid and methacrylic acid; and carboxyalkyl(meth)acrylates such as 2-carboxyethyl(meth)acrylate, and 3-carboxypropyl(meth) acrylate. Still other suitable acidic monomers include (meth) acryloylamino acids, such as those described in U.S. Pat. No. 4,157,418 (Heilmann). Exemplary (meth)acryloylamino acids include, but are not limited to, N-acryloylglycine, N-acryloylaspartic acid, N-acryloyl-β-alanine, and 2-acrylamidoglycolic acid. Salts of any of these acidic monomers can also be used.

Some exemplary ionic grafting monomers that are capable of providing a positive charge (at a selected pH) are amino (meth)acrylates or amino (meth)acrylamides of Formula 7 or quaternary ammonium salts thereof. The counterions of the quaternary ammonium salts are often halides, sulfates, phosphates, nitrates, and the like.

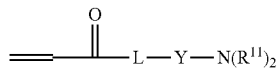

where L is —O— or —NR$^3$—, where R$^3$ is H or C$_1$-C$_4$ alkyl-; and Y is an alkylene (e.g., an alkylene having 1 to 10 carbon atoms, 1 to 6, or 1 to 4 carbon atoms). Each R$^{11}$ is independently hydrogen, alkyl, hydroxyalkyl (i.e., an alkyl substituted with a hydroxy), or aminoalkyl (i.e., an alkyl substituted with an amino). Alternatively, the two R$^{11}$ groups taken together with the nitrogen atom to which they are attached can form a heterocyclic group that is aromatic, partially unsaturated (i.e., unsaturated but not aromatic), or saturated, wherein the heterocyclic group can optionally be fused to a second ring that is aromatic (e.g., benzene), partially unsaturated (e.g., cyclohexene), or saturated (e.g., cyclohexane).

In some embodiments of Formula 7, both R$^{11}$ groups are hydrogen. In other embodiments, one R$^{11}$ group is hydrogen and the other is an alkyl having 1 to 10, 1 to 6, or 1 to 4 carbon atoms. In still other embodiments, at least one of R$^{11}$ groups is a hydroxy alkyl or an amino alkyl that have 1 to 10, 1 to 6, or 1 to 4 carbon atoms with the hydroxy or amino group being positioned on any of the carbon atoms of the alkyl group. In yet other embodiments, the R$^{11}$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to imidazolyl. The heterocyclic group can be fused to an additional ring such as a benzene, cyclohexene, or cyclohexane. Exemplary heterocyclic groups fused to an additional ring include, but are not limited to, benzoimidazolyl.

Exemplary amino acrylates (i.e., L in Formula 7 is —O—) include N,N-dialkylaminoalkyl acrylates such as, for example, N,N-dimethylaminoethylacrylate, N,N-dimethylaminoethylmethacrylate, N,N-diethylaminoethyl acylate, N,N-diethylaminoethylmethacrylate, N,N-dimethylaminopropylacrylate, N,N-dimethylaminopropylmethacrylate, N-tert-butylaminopropylmethacrylate, N-tert-butylaminopropylacrylate and the like.

Exemplary amino (meth)acrylamides, (i.e., L in Formula 7 is —NR$^3$—) include, for example, N-(3-aminopropyl)methacrylamide, N-(3-aminopropyl)acrylamide, N-[3-(dimethylamino)propyl]methacrylamide, N-(3-imidazolylpropyl) methacrylamide, N-(3-imidazolylpropyl)acrylamide, N-(2-imidazolylethyl)methacrylamide, N-(1,1-dimethyl-3-imidazoylpropyl)methacrylamide, N-(1,1-dimethyl-3-imidazoylpropyl)acrylamide, N-(3-benzoimidazolylpropyl) acrylamide, and N-(3-benzoimidazolylpropyl) methacrylamide.

Exemplary quaternary salts of the ionic monomers of Formula 7 include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Other monomers that can provide positively charged groups (at a selected pH) to the base substrate include the dialkylaminoalkylamine adducts of alkenylazlactones (e.g., 2-(diethylamino)ethylamine, (2-aminoethyl)trimethylammonium chloride, and 3-(dimethylamino)propylamine adducts of vinyldimethylazlactone) and diallylamine monomers (e.g., diallylammonium chloride and diallyldimethylammonium chloride). Other examples include the quaternary salt of dimethylaminoethyl methacrylate.

Neutral hydrophilic monomers that may be incorporated are poly(alkylene oxide) monomers having a (meth)acryloyl or non-acryloyl ethylenically unsaturated group and a non-polymerizable terminus. Such monomers may be of the formula 8:

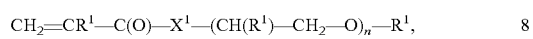

wherein each R$^1$ is independently H or C$_1$-C$_4$ alkyl, X$^1$ is —O— or —NR$^3$—, where R$^3$ is H or C$_1$-C$_4$ alkyl and n is 2 to 100.

Others include the alkenylazlactones adducts of polyetheramines (such as the monoamine, diamine and triamines based on the polyetheramine structure). One example of these compounds is the Jeffamine® series, from Huntsman, The Woodlands, Tex., USA.

Such optional hydrophilic comonomers are used in amounts of about 1% to about 70% by weight, preferably of about 5% to about 50% by weight, relative to the total monomer weight.

The ligand functional substrate may be prepared as shown in the following Scheme 1. Here, a polyamino polymer (I) is crosslinked by the polyfunctional crosslinking agent R$^8$(Z)$_y$ of Formula 1 to form the crosslinked polymer (II). A portion of the unreacted amino groups of the polyamino polymers are then functionalized with a (meth)acryloyl compound having an amine-reactive functional group of Formula 2 to produce a crosslinked polyamino polymer having pendent ethylenically unsaturated groups (III). In the presence of a free-radical catalyst, polymerization is initiated in the presence of the ligand—functional (meth)acryloyl monomer of Formula 3 to produce an amino polymer having grafted ligand groups (IV) having "z" polymerized groups. Note with respect to the following Schemes, the grafted polymer may have additional hydrophilic monomer units as described supra.

It will be understood with respect to Scheme 1 that the reactions of the polyamine polymer with the polyfunctional crosslinking agent and with the amine-reactive monomer are shown sequentially for clarity, but may occur essentially simultaneously (i.e., during the coating and drying process). It will be further understood that the hydrophilic monomers and multifunctional acrylates are omitted from the Scheme for clarity, and the ligand-function monomer of Formula 3 is simplified for clarity.

Scheme 1

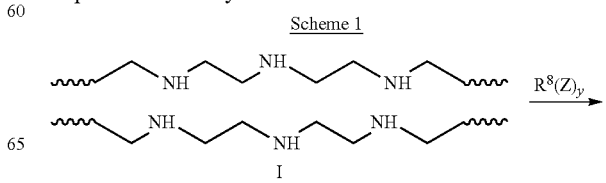

I

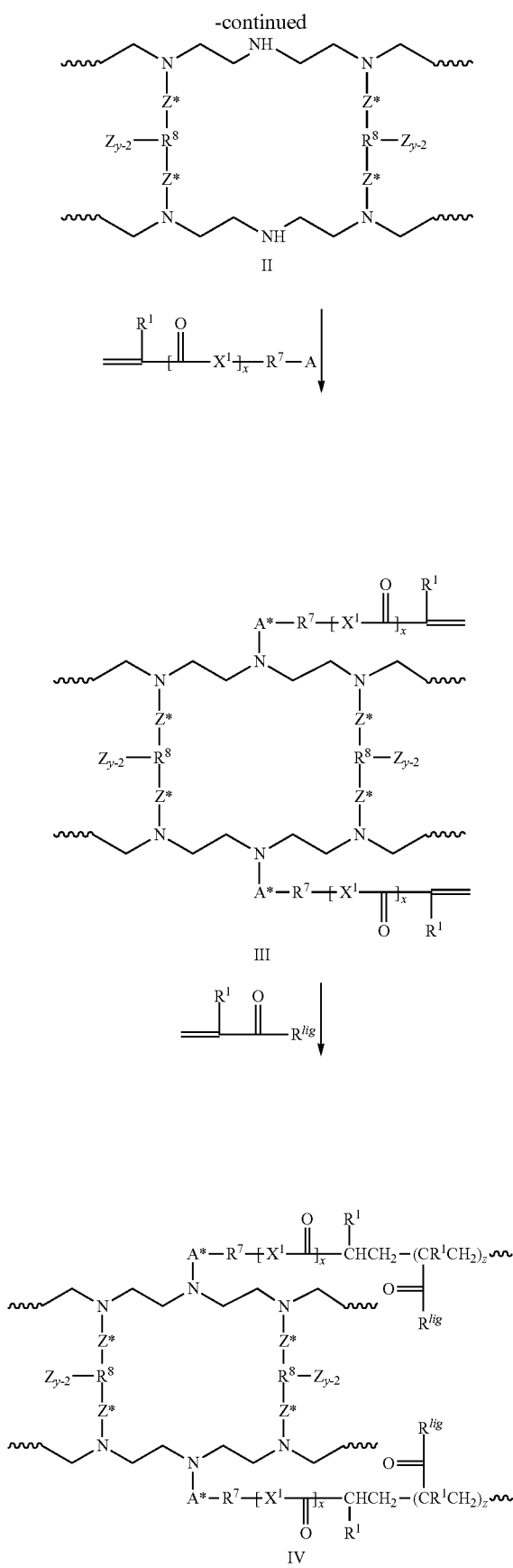

In the reactions of Scheme 1, the ligand groups are directly grafted with the ligand functional monomers. Alternatively, the crosslinked polyamino polymer may be indirectly functionalized with ligand groups, by grafting the intermediate III with a monomer having an alkenyl group and a functional group capable of reacting with a ligand compound. Such functionalized monomers are of the formula 9:

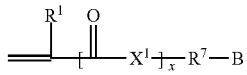

9 where $X^1$ is —O— or —NR$^1$—, where $R^1$ is H or $C_1$-$C_4$ alkyl, $R^1$ is H or $C_1$-$C_4$ alkyl;

$R^7$ is a single bond or a (hetero)hydrocarbyl linking group,

B is a nucleophilic or electrophilic functional group that is reactive with ligand compound, such as those of Formulas 5a-b, and x is 0 or 1.

In some embodiments there is the proviso that when x is 0, then $R^7$ is a (hetero)hydrocarbyl linking group. Generally when x is 0, then $R^7$ is a covalent bond.

It will be understood that the functional monomers of formula 9 may be inclusive with those of Formula 2. Generally the "B" group will not react readily with the amino groups of the primer layer. The B functional group may further contain nucleophilic or electrophilic groups, including halo, hydroxyl, amino (especially secondary amino), ketone (such as acetyl) carboxyl, aziridinyl, vinyloxy, and oxazolinyl, that are reactive toward, and will form a covalent bond with a ligand compound for incorporating ligand groups into the article. In Scheme 2, the B* moiety is that group formed from the B functional group and the ligand compound. For example, if B is an acetyl group, and the ligand compound has an amine group, B* will be an imine group.

In some embodiments, the intermediate III of Scheme 2 is reacted with a carbonyl functional monomer, to provide a grafted copolymer having pendent carbonyl groups, i.e. the B group of Formula 9 contains a carbonyl group. The grafted polymer comprises polymerized monomer units of an ethylenically unsaturated monomer having a carbonyl group, preferably a ketone or aldehyde group.

Generally, the carbonyl-functional (co)polymer comprises polymerized monomer units of the monomers selected from the group consisting of: acrolein, vinyl methyl ketone, vinyl ethyl ketone, vinyl isobutyl ketone, isopropenyl methyl ketone, vinyl phenyl ketone, diacetone (meth)acrylamide, acetonyl acrylate, and diacetone (meth)acrylate (co)polymers. Where B is a carbonyl group, and the ligand compound is attached with an amine group, B* will be an imine group.

The pendent carbonyl group then may be functionalized by nucleophilic groups, typically an amine group to provide the requisite ligand group. For example the polymer of Scheme 2 having grafted carbonyl groups may be subsequently functionalized with the guanidinyl compound of Formula 5. This reaction typically requires the addition of an acid catalyst.

As with Scheme 1, the reactions are shown sequentially for clarity, but may occur essentially simultaneously (i.e., during the coating and drying process). It will be further understood that the hydrophilic monomers and multifunctional acrylates are omitted from the Scheme for clarity.

Scheme 2

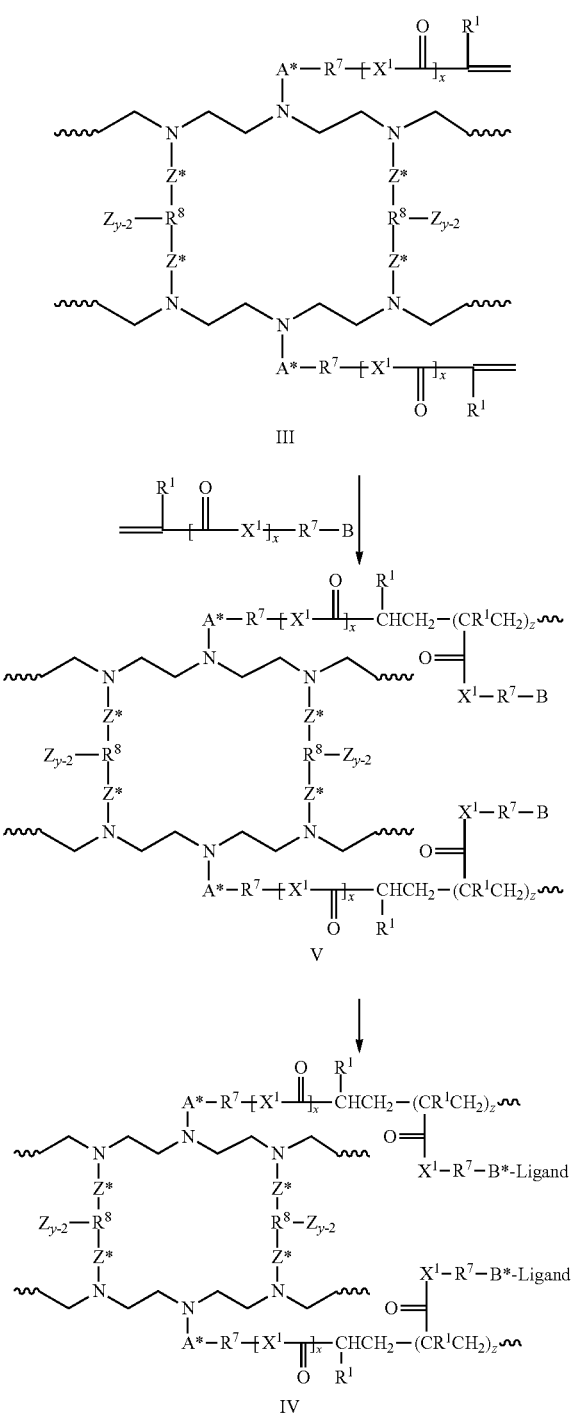

By either reaction scheme, a primed substrate is provided with a grafted polymer of the formula 10:

$$-(M^{Lig})_y-(M^{Hydrophil})_x-(M^{crosslink})_z-, \quad 10$$

where ($M^{Hydrophil}$)$_x$ are hydrophilic monomer units having "x" polymerized monomer units, ($M^{Lig}$)$_y$ are ligand functional monomer units having "y" polymerized monomer units, ($M^{crosslink}$)$_z$ are multifunctional (meth)acrylate monomer units having "z" polymerized monomer units, y is 10 to 100 wt. % of the monomer units;

x is 0 to 90 wt. % of the monomer units;

z is 0 to 5 wt. % of the monomer units.

It will be understood the monomer units are simplified for clarity. It is believed that the multifunctional acrylate will crosslink the grafted ligand functional polymer, and/or will further provide grafted hyperbranched polymers with ligand functional groups. It is further believed that free, ungrafted polymer may be present on the surface of the substrate, which may further be crosslinked and/or hyperbranched to the extent that it is physically entangled with the grafted copolymer.

The substrate may be in any form such as particles, fibers, films or sheets. Suitable particles include, but are not limited to, organic particles, inorganic particles, and porous and non-porous particles. Preferably the base substrate is porous. Suitable porous base substrates include, but are not limited to, porous particles, porous membranes, porous nonwoven webs, and porous fibers The substrate may be formed from any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), polyesters such as poly(lactic acid), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

In some embodiments, the thermoplastic polymer may be surface treated, such as by plasma discharge, to provide suitable functionality to the surface of the substrate. Surface treatment provides functional groups such as hydroxyl groups that can improve wetting by the primer solution. One such useful plasma treatment is described in U.S. Pat. No. 7,125,603 (David et al.).

Suitable polyolefins include, but are not limited to, poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly(iminoadipolyliminohexamethylene), poly(iminoadipolyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

A preferred substrate is a porous substrate that is a microporous membrane such as a thermally-induced phase separation (TIPS) membrane. TIPS membranes are often prepared by forming a solution of a thermoplastic material and a second material above the melting point of the thermoplastic material. Upon cooling, the thermoplastic material crystallizes and phase separates from the second material. The crystallized material is often stretched. The second material is optionally removed either before or after stretching. Microporous membranes are further disclosed in U.S. Pat. No. 4,529,256 (Shipman); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and U.S. Pat. No. 5,962,544 (Waller, Jr.). Some exemplary TIPS membranes comprise poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. For some applications, a TIPS membrane comprising PVDF is particularly desirable. TIPS membranes comprising PVDF are further described in U.S. Pat. No. 7,338,692 (Smith et al.).

The substrate may be in any form such as films or sheets. Preferably the base substrate is porous. Suitable porous base substrates include, but are not limited to, porous membranes, porous nonwoven webs, and porous fibers.

In many embodiments, the base substrate has an average pore size that is typically greater than about 0.2 micrometers in order to minimize size exclusion separations, minimize diffusion constraints and maximize surface area and separation based on binding of a target molecule. Generally, the pore size is in the range of 0.1 to 10 micrometers, preferably 0.5 to 3 micrometers and most preferably 0.8 to 2 micrometers when used for binding of viruses. The efficiency of binding other target molecules may confer different optimal ranges.

In another exemplary embodiment the porous bases substrate comprises a nylon microporous film or sheet, such as those described in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinacchio et al.), U.S. Pat. Nos. 3,928,517, 4,707,265 (Knight et al.), and U.S. Pat. No. 5,458,782 (Hou et al.).

In other embodiments, the porous base substrate is a nonwoven web which may include nonwoven webs manufactured by any of the commonly known processes for producing nonwoven webs. As used herein, the term "nonwoven web" refers to a fabric that has a structure of individual fibers or filaments which are randomly and/or unidirectionally interlaid in a mat-like fashion.

For example, the fibrous nonwoven web can be made by wet laid, carded, air laid, spunlaced, spunbonding or meltblowing techniques or combinations thereof. Spunbonded fibers are typically small diameter fibers that are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to from a web of randomly dispersed meltblown fibers. Any of the non-woven webs may be made from a single type of fiber or two or more fibers that differ in the type of thermoplastic polymer and/or thickness.

Further details on the manufacturing method of non-woven webs of this invention may be found in Wente, Superfine Thermoplastic Fibers, 48 INDUS. ENG. CHEM. 1342 (1956), or in Wente et al., Manufacture Of Superfine Organic Fibers, (Naval Research Laboratories Report No. 4364, 1954).

In the process of forming the articles of the invention, the base substrate is first coated with the primer solution. For ease of manufacturing and reduced manufacturing costs, it is desirable to coat, crosslink, and functionalize the polyamine primer all in one operation. This one-step operation also has the advantage that the stoichiometry of crosslinking and functionalization can be readily controlled. Useful coating techniques include applying an aqueous solution or dispersion of the primer components onto the base substrate, followed by evaporating the solvent to form the primer coating. Coating methods include the techniques commonly known as dip, spray, knife, bar, slot, slide, die, roll, or gravure coating.

Coating quality generally depends on mixture uniformity, the quality of the deposited liquid layer, and the process used to dry or cure the liquid layer. Coating quality of the primer layer is especially important since there are typically few or no chemical bonds between the substrate and the primer, and the primer layer is advantageous for subsequent grafting of the ligand-functionalized polymer layer. Coating quality may sometimes be improved by including alcohol cosolvents, especially with hydrophobic base substrates, as this improves the wetting of the substrate with the primer solution and thus ensures a more continuous coating. Improved crosslinking, leading to increased durability of the primer coating, and improved covalent attachment of the alkenyl group, leading to more efficient grafting, may sometimes be accomplished by increasing the drying temperature.

Although the total concentration of reactants (polyamine polymer, crosslinking agent, and amine reactive monomer 2) in the primer solution may vary widely, it is generally desirable to keep that concentration fairly low so as to minimize the thickness of the primer layer. Typically, the total concentration of reactants is from about 0.1% to about 5% by weight, from about 0.25% to about 2% by weight, or from about 0.5% to about 1.5% by weight based on the total weight of the primer solution. These concentrations will typically lead to about 0.5% to about 3% weight gain in the substrate upon priming.

In the second step of the process, the ligand-functionalized monomer is graft (co)polymerized onto the alkenyl modified primer layer. Typically, the primed substrate is coated with an imbibing solution comprising the ligand-functionalized monomer, any comonomers, an initiator, and a solvent for the mixture.

The polymerization may be initiated with either a thermal initiator or photoinitiator, preferably a photoinitiator. Any conventional free radical initiator may be used to generate the initial radical. Examples of suitable thermal initiators include peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2,-azo-bis(isobutyronitrile), and t-butyl perbenzoate. Examples of commercially available thermal initiators include initiators available from DuPont Specialty Chemical (Wilmington, Del.) under the VAZO trade designation including VAZO™ 67 (2,2'-azo-bis(2-methylbutyronitrile)) VAZO™ 64 (2,2'-azo-bis(isobutyronitrile)) and VAZO™ 52 (2,2'-azo-bis(2,2-dimethylvaleronitrile)), and Lucidol™ 70 from Elf Atochem North America, Philadelphia, Pa.

Useful photoinitiators include benzoin ethers such as benzoin methyl ether and benzoin isopropyl ether; substituted acetophenones such as 2,2-dimethoxyacetophenone, available as Irgacure™ 651 photoinitiator (Ciba Specialty Chemicals), 2,2 dimethoxy-2-phenyl-1-phenylethanone, available as Esacure™ KB-1 photoinitiator (Sartomer Co.; West Chester, Pa.), 1-[4-(2-hydroxyethoxy)phenyl]-2-hydroxy-2-methyl-1-propan-1-one, available as Irgacure™ 2959 (Ciba Specialty Chemicals), and dimethoxyhydroxyacetophenone; substituted α-ketols such as 2-methyl-2-hydroxy propiophenone; aromatic sulfonyl chlorides such as 2-naphthalenesulfonyl chloride; and photoactive oximes such as 1-phenyl-1,2-propanedione-2-(O-ethoxy-carbonyl)oxime. Particularly preferred among these are the substituted acetophenones, and especially 1-[4-(2-hydroxyethoxy)phenyl]-2-hydroxy-2-methyl-1-propan-1-one due to its water solubility. A particularly useful polymerizable photoinitiator is one:one adduct of 2-vinyl-4,4-dimethylazlactone with Irgacure™ 2959, prepared as disclosed in Example 1 of U.S. Pat. No. 5,506,279 (Babu et al.), incorporated herein by reference The initiator is used in an amount effective to facilitate free radical addition of the monomer(s) to pendent ethylenically unsaturated groups on the crosslinked polyamine polymer (derived from the amine reactive monomer, component b)3)) and the amount will vary depending upon, e.g., the type of initiator, and the molecular weight of the polymer and the degree of functionalization desired. The initiators can be used in amounts from about 0.001 part by weight to about 5 parts by weight based on 100 parts total monomer.

The solvent may be any polar solvent. In many embodiments the solvent is water or a water/water-miscible organic solvent mixture. The ratio of water to organic solvent can vary widely, depending upon monomer solubility. With some monomers, it is typically greater than 1:1 (v/v) water to organic solvent, preferably greater than 5:1, and more preferably greater than 7:1. With other monomers, a higher proportion of organic solvent, even up to 100%, with some alcohols especially, may be preferred.

Any such water miscible organic solvent preferably has no groups that would retard the polymerization. In some embodiments, the water miscible solvents are protic group containing organic liquids such as the lower alcohols having 1 to 4 carbon atoms, lower glycols having 2 to 6 carbon atoms, and lower glycol ethers having 3 to 6 carbon atoms and 1 to 2 ether linkages. In some embodiments higher glycols such as poly(ethylene glycol) may be used. Specific examples are methanol, ethanol, isopropanol, n-butanol, t-butyl alcohol, ethylene glycol, methoxyethanol, ethoxyethanol, propoxyethanol, butoxyethanol, methyl carbitol, ethyl carbitol, and mixtures thereof.

In other embodiments, non-protic water miscible organic solvents that can also be used such as aliphatic esters and ketones and sulfoxides methoxyethyl acetate, ethoxyethyl acetate, propoxyethyl acetate, butoxyethyl acetate, triethyl phosphate, acetone, methyl ethyl ketone, methyl propyl ketone and dimethyl sulfoxide.

In embodiments where the polymer is functionalized in aqueous or other protic solvents, the "A" amine-reactive groups should be selected to be sufficiently stable under the reaction conditions so the "A" groups primarily react with the amine groups of the polyamine.

The concentration of each component in the solution may vary depending on a number of factors including, but not limited to, the grafting monomer or monomers in the imbibing solution, the extent of grafting desired, the reactivity of the grafting monomer(s), and the solvent used. Typically, the total concentration of the monomers in the imbibing solution ranges from about 0.1 wt % to about 60 wt %, desirably, from about 1 wt % to about 35 wt %, more desirably, from about 5% to about 25%, based on a total weight of the solution. Following grafting, washing, and drying, typical total weight gains by the substrate are in the range of about 5% to about 30%, in the range of about 10% to about 25%, or in the range of about 12% to about 20%.

The method of grafting a ligand functionalized polymer to the surface of the substrate alters the original nature of the base substrate, as the substrate bears a grafted coating of the ligand functional polymer. The present invention enables the formation of ligand functionalized polymer substrates having many of the advantages of a base substrate (e.g., mechanical and thermal stability, porosity), but with enhanced affinity for biological species such as viruses, resulting from the monomers and steps used to form a given functionalized substrate. While not wanting to be bound by theory, it is believed that the grafted, tentacular nature of the current coatings are responsible, at least in part, for the improved binding capacities for biological species over materials in the prior art.

The porous substrates having a coating of ligand-functionalized polymer are particularly suited as filter media, for the selective binding and removal of target biological species including proteins, cells, cell debris, microbes, nucleic acids, and/or viruses from biological samples. The present disclosure further provides a method for the removal of target biological species from a biological sample by contacting the sample with the ligand polymer functionalized substrate as described herein. As used herein "target biological species" may include a contaminant or a species of interest.

The ligand functionalized substrate is useful for the purification of biological or other fluid samples comprising biologically derived species (biological species). Biological species include, but are not limited to, cells, cell debris, proteins, nucleic acids, endotoxins, and viruses. Cells and cell debris include those derived from archaea, bacteria, and eucaryota. Bacteria include, but are not limited to, Gram-negatives such as *Pseudomonas* species, *Escherichia coli, Helicobacter pylori,* and *Serratia marcesens*; Gram-positives such as *Staphylococcus* species, *Enterococcus* species, *Clostridium* species, *Bacillus* species, and *Lactobacillus* species; bacteria that do not stain traditionally by Gram's method such as *Mycobacterium* species, and non-vegetative forms of bacteria such as spores. Eucaryota include, but are not limited to, animal cells, algae, hybridoma cells, stem cells, cancer cells, plant cells, fungal hyphae, fungal spores, yeast cells, parasites, parasitic oocysts, insect cells, and helminthes. Proteins, include, but are not limited to, natural proteins, recombinant proteins, enzymes, and host cell proteins. Viruses include, but are not limited to, enveloped species such as Herpesviruses, Poxviruses, Adenoviruses, Papovaviruses, Coronaviruses, retroviruses such as HIV, and Plasmaviridae; and non-enveloped species such as Caliciviridae, Corticoviridae, Myoviridae, and Picornaviridae.

In some embodiments, the biological species being removed from the fluid is the object of the purification. For example, a recombinant protein or enzyme may be prepared in cell culture or by fermentation, and the substrate can be used to capture the protein or enzyme as the first step in the purification process. In another example, the substrate may be used to capture microorganisms from a fluid as the first step in a process of concentrating, enumerating, and/or identifying the microorganisms.

In other embodiments, the biological species being removed from the fluid is a contaminant that must be removed prior to additional processing steps for the fluid.

Significantly, many of the ligand functional substrates are useful under conditions of high salt concentration or high ionic strength, i.e., they are "salt tolerant". The term "salt" is meant to include all low molecular weight ionic species which contribute to the conductivity of the solution. The importance of utility of the ligand functional substrates in the presence of salt is that many process solutions used in biopharmaceutical or enzyme manufacture have conductivities in the range of 15-30 mS/cm (approximately 150-300 mM salt) or more. Salt tolerance can be measured in comparison to that of the conventional quaternary amine or Q ligand (e.g. trimethylammonium ligand), whose primarily electrostatic interactions with many biological species rapidly deteriorates at conductivities three- to six-fold less than the target range of 15-30 mS/cm. For example, membranes derivatized with the conventional Q ligand exhibit a drop in φX174 viral clearance from a six log-reduction value (LRV) to a one (1) LRV in going from 0 to 50 mM NaCl (ca. 5-6 mS/cm conductivity). Viruses such as φX174 which have pIs close to 7 (are neutral or near-neutral at pH 7) are extremely difficult to remove from process streams. Similar problems are observed when attempting to remove other biological species from process fluids. For example, when attempting to remove positively charged proteins such as host cell proteins through the use of filtration devices functionalized with conventional Q ligands, the process fluid may have to be diluted two-fold or more in order to reduce the conductivity to an acceptable range. This is expensive and dramatically increases the overall processing time. Surprisingly, it has been found that ligand functionalized substrates in which the ligands comprise guanidine or biguanide groups perform extremely well under high ionic strength conditions.

The biological sample is contacted with the ligand functionalized substrate for a time sufficient to interact and form a complex with the target biological species disposed (dissolved or suspended) in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 50% of its original concentration. It is more preferred that the solution is contacted with the ligand functionalized substrate for a time sufficient to interact and form a complex with the target biological species disposed in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 10% of its original concentration. It is still more preferred that the solution is contacted with the ligand functionalized substrate for a time sufficient to interact and form a complex with the target biological species disposed in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 1% of its original concentration.

EXAMPLES

Test Methods
Static BSA Capacity Test for Membranes

Disks measuring 24 mm in diameter were punched out of the membranes and placed in 5 mL centrifuge tubes. Bovine serum albumin solution (BSA; Catalog #A-7906; Sigma Aldrich; St. Louis Mo.) was prepared to a concentration of about 3.0 mg/ml in 25 mM TRIS (tris(hydroxymethyl)aminomethane; Sigma Aldrich; St. Louis Mo.) buffer, pH 8.0 and 4.5 ml of the BSA solution was pipetted into each centrifuge tube. The tubes were capped, and tumbled overnight (typically 14 hours). The supernatant solutions were analyzed using a UV-VIS spectrometer at 279 nm (with background correction applied at 325 nm). The static binding capacities for the samples were determined by comparison to the absorption of the starting BSA solution, and are reported in mg/mL as the average of three replicates.

Dynamic BSA Capacity Test for Membranes:

The membranes were analyzed for binding of proteins by passing solutions of the test analytes through a 6-layer stack of the membranes punched out into 25-mm diameter disks and placed in a 25 mm diameter holder attached to an AKTA chromatography system (GE Healthcare, NY). Bovine serum albumin (BSA) was prepared at a concentration 1 mg/mL in 25 mM TRIS buffer, pH 8. The BSA feed solution was pumped through the membrane stack at a flow rate of 1 mL/min and the UV absorbance of the effluent was monitored at a wavelength of 280 nm. The dynamic binding capacity of the membrane was evaluated using standard chromatography techniques, and reported in mg/mL at 10% breakthrough.

Preparation of Primed Nylon Membrane

Polyethylenimine (PEI—MW 70,000, a 30% by weight aqueous solution, Cat#00618; Polysciences, Inc.; Warrington Pa.) was diluted to 1.0% solids with IPA (isopropanol). A 50 gram portion of this solution was formulated with enough butanediol diglycidyl ether (BUDGE, Sigma Aldrich) to react with 5% of the amine groups of the polymer and enough glycidylmethacrylate (GMA, Sigma Aldrich) to react with 10% of the amine groups. Primed membranes were prepared by dipping a 10 centimeter square piece of a nylon 66 membrane (single reinforced layer nylon three zone membrane, nominal pore size 1.8 µm, #080ZN from 3M Purification, Inc.; Meriden Conn.), into the coating solution, removing excess coating solution with a #14 wire-wound coating rod, then allowing the membrane to air dry at ambient temperature for at least 15 minutes.

Examples 1-5, Comparative Examples C1-C2

Coating solutions (100 grams total weight) were prepared by dissolving DAAm (diacetoneacrylamide; Alfa Aesar; Ward Hill Mass.) in the amounts listed in Table 1, 0.05 gram MBA (methylenebisacrylamide; Sigma Aldrich), and 0.5 gram photoinitiator (Irgacure® 2959; Ciba; Basel, Switzerland) in deionized water. Sheets of primed nylon membrane were dip coated with the coating solutions of Examples 1-5 and sandwiched between two sheets of polyester film. The excess coating solution was removed using a #14 wire-wound coating rod and the sheets were irradiated using a blacklight UV source for 15 minutes. The sheets were turned over, and the opposite side was also exposed to the UV source for 15 minutes. The polyester sheets were removed, and the grafted membranes were placed in 500 mL polyethylene bottles. A 0.5 M aminoguanidine solution was prepared by dissolving 6.15 grams of AG (Aminoguanidine sulfate; Alfa Aesar) in 100 mL of deionized water and adding 0.2 mL of concentrated hydrochloric acid, and added to each bottle. The membranes were allowed to react with the aminoguanidine solution overnight, then the excess solution was poured off. The bottles were filled with deionized water and shaken for 30 minutes to wash off residual monomer or ungrafted polymer. The water was replaced with 50 mM sodium acetate, pH 4.5, and washed for 30 minutes, washed another 30 minutes with deionized water, and then allowed to dry. Samples were analyzed for static and dynamic BSA capacities (Table 1).

Comparative Example C1 was the primed membrane.

Comparative Example C2 was a membrane prepared similarly to Example 3 but without reacting with aminoguanidine. Comparative Examples were tested for static BSA capacity.

TABLE 1

| Example | DAAm (grams) | BSA Capacity (mg/mL) | |
| --- | --- | --- | --- |
| | | Static | Dynamic |
| 1 | 1 | 14 | NM |
| 2 | 3 | 53 | 26 |
| 3 | 5 | 104 | 43 |
| 4 | 7 | 129 | 19 |
| 5 | 10 | 54 | 0 |
| Comp. 1 | 0 | 25 | NM |
| Comp. 2 | 5 | 0 | NM |

NM = Not Measured

Examples 6-9

Coating solutions were prepared at 5% total solids, according to the procedure described above for Example 3, except that a co-monomer, DMA (Dimethylacrylamide, Sigma Aldrich), replaced a portion of the DAAm as shown in Table 2. Primed membranes were likewise coated, UV grafted, reacted with aminoguanidine, and washed, and tested for Static BSA Capacity (Table 2).

TABLE 2

| Example | DAAm (grams) | DMA (grams) | Static BSA Capacity (mg/mL) |
| --- | --- | --- | --- |
| 6 | 4.75 | 0.25 | 90 |
| 7 | 4.5 | 0.5 | 85 |
| 8 | 4.25 | 0.75 | 78 |
| 9 | 4.0 | 1.0 | 63 |

Examples 10-11

Coating solutions were prepared at 5% solids according to the procedure described in Example 3. Example 10 was coated and grafted on a primed membrane, as in Example 3, while Example 11 was coated and grafted on an unprimed membrane (#080ZN from 3M Purification, Inc). The grafted membranes were reacted with aminoguanidine as in Example 3, except that the aminoguanidine sulfate solution was prepared at a 2.0 M concentration. Static BSA capacities were measured to be 97 and 88 mg/mL, respectively, for Examples 10 and 11.

Examples 12-17

Preparation of 4-(2-(methacryloyloxy)ethylaminocarbonylamino)butyl guanidinium triethylammonium sulfate (IEM-AGM triethylammonium sulfate)

Solution: A solution of agmatine sulfate (12.0 g, 53 mmol) dissolved in 20 mL of deionized water was treated with triethylamine (7.31 mL, 53 mmol) and 10 mL of methanol. The solution was then placed in a cold water bath (approximately 15° C.) and 2-isocyanatoethyl methacrylate (7.50 mL, 53 mmol) was added dropwise. The solution was allowed to stir for 90 min after which time NMR showed complete conversion to 4-(2-(methacryloyloxy)ethylaminocarbonylamino) butyl guanidinium triethylammonium sulfate. The mixture was diluted to 100 grams total by addition of methanol (46.5 grams). $^1$H NMR (500 MHz, D$_2$O) δ 6.02 (s, 1H), 5.61 (s, 1H), 4.11 (m, 2H), 3.33 (m, 2H), 3.06 (m, 2H), 3.04-2.98 (m, 8H), 1.81 (s, 3H), 1.55-1.37 (m, 4H), 1.14 (t, J=7.3 Hz, 9 H).

Solid: A solution was prepared by dissolving 50 g of agmatine sulfate (50 g) in 500 mL of deionized water in a reaction flask followed by stirring in 200 mL of acetone and 40 mL triethylamine (287 mmol). The flask was placed in a room temperature water bath while 40 mL of IEM (2-isocyanatoethyl methacrylate (283 mmol)) was slowly added by drops over 5 minutes. The solution was stirred vigorously for 4 hours during which a white precipitate formed. The precipitate was filtered out and acetone was removed from the filtered solution in a Rotovap. The remaining solution was washed three times with ethyl acetate and once with methylene chloride. Both solvents caused phase separation and the solvent phase was decanted. The remaining liquid was freeze dried to form 36 grams of white crystalline IEM-AGM. Multiple lots of IEM-AGM were synthesized. $^1$H NMR (500 MHz, CD$_3$OD) indicated differing levels of purity on a batch by batch basis: Lot A had a purity of 79%, Lot B had a purity of 87%, and Lot C had a purity of 90%. For Lots A and C, the starting agmatine sulfate had a purity of 77 weight percent. A recrystallized agmatine sulfate having a purity of about 80% was used for Lot B.

Six coating solutions, each having a total weight of 5 g, were prepared by dissolving 1.11 grams IEM-AGM Lot C (nominally 90% pure by NMR) and 0.01 grams MBA (N,N'-Methylene bisacrylamide; Sigma Aldrich) in deionized water. A photoinitiator solution was prepared by dissolving 5.0 grams Photoinitiator (IRGACURE 2959; BASF; Florham Park N.J.) in ethanol to a total volume of 25 mL. Varying amounts of the photoinitiator solution (Table 3) were delivered by micropipette to each of the six coating solutions and mixed until homogeneous. Primed membranes were placed on a sheet of polyester film, coated by pipetting approximately 4.5 mL of each solution to the top surface of the membrane, and allowing to soak for about 2 minutes before a second sheet of polyester was placed on top of the membrane. Excess coating solution was removed using a #14 wire-wound coating rod, and the sandwich was irradiated using a blacklight UV source for 15 minutes on each side as in Example 1. Grafted membranes were washed, dried, and evaluated for BSA binding capacities according to the procedure described in Example 1 (Table 3).

TABLE 3

| Example | Photoinitiator (μL) | BSA Capacity (mg/mL) | |
| --- | --- | --- | --- |
| | | Static | Dynamic |
| 12 | 250 | 77 | NM |
| 13 | 125 | 91 | NM |
| 14 | 62.5 | 89 | 51 |
| 15 | 31.2 | 92 | 49 |
| 16 | 15.6 | 99 | 51 |
| 17 | 7.8 | 95 | NM |

NM = Not Measured

Example 18

A coating solution was prepared as in Example 15, except that IEM-AGM used was Lot B (nominally 87% purity), and the solvent was 33/67 deionized water/isopropanol by volume. A primed nylon membrane was coated, grafted, washed, and dried according to the procedures described in Example 1. The static BSA capacity was determined to be 98 mg/mL.

Examples 19-28

Coating solutions weighing a total of 5 grams were prepared by dissolving IEM-AGM (Lot 25A) and a co-monomer in the amounts listed in Table 4, and 1% by weight MBA based on the amount of IEM-AGM) in 50/50 deionized water/isopropanol by volume, and adding 62.5 μL of photoinitiator solution prepared as described in Example 14. The co-monomers were HEMA (Hydroxy ethyl methacrylate; Sigma Aldrich), MAPTAC (Methacrylamidopropyltrimethyl-ammonium chloride monomer—50% by weight in aqueous solution; TCI America; Portland Oreg.); AMPS-Na (Sodium salt of 2-acrylamido-2-methyl-1-propanesulfonic acid, 50 weight % solution—AMPS 2405; Lubrizol Corp.; Wickliffe Ohio); and DMA. Primed membranes were coated, grafted, washed, and dried as in Example 1. Results are shown in Table 4.

TABLE 4

| | IEM-AGM | Co-monomer | | BSA Capacity (mg/mL) | |
|---|---|---|---|---|---|
| Ex | (grams) | Co-monomer | (grams) | Static | Dynamic |
| 19 | 0.5 | None | 0 | 83 | NM |
| 20 | 0.55 | HEMA | 0.06 | 102 | 52 |
| 21 | 0.63 | HEMA | 0.13 | 126 | 68 |
| 22 | 0.71 | HEMA | 0.21 | 131 | 85 |
| 23 | 0.71 | MAPTAC | 0.21 | 81 | 38 |
| 24 | 0.83 | MAPTAC | 0.33 | 101 | 54 |
| 25 | 0.63 | AMPS-Na | 0.13 | 116 | 68 |
| 26 | 0.71 | AMPS-Na | 0.21 | 128 | 16 |
| 27 | 0.71 | DMA | 0.21 | 103 | 59 |
| 28 | 0.83 | DMA | 0.33 | 123 | 1 |

NM = Not Measured

Examples 29-39

Coating solutions weighing a total of 5 grams were prepared by dissolving IEM-AGM Lot C (nominally 90% purity) and PEG400MA (Polyethyleneglycol 400 monomethacrylate co-monomer; Polysciences, Inc.) in the amounts listed in Table 5, and 1% MBA by weight, based on the amount of IEM-AGM, in 50/50 deionized water/isopropanol by volume, and adding 62.5 μL of the photoinitiator solution of Example 14. Primed nylon membranes were coated, grafted, washed, dried and tested as described in Example 1. Results are shown in Table 5.

TABLE 5

| | IEM-AGM | Comonomer | BSA Capacity (mg/mL) | |
|---|---|---|---|---|
| Example | (grams) | (grams) | Static | Dynamic |
| 29 | 0.55 | 0.06 | 115 | 49 |
| 30 | 0.63 | 0.13 | 126 | 68 |
| 31 | 0.71 | 0.21 | 102 | 100 |
| 32 | 0.71 | 0.29 | 130 | 108 |
| 33 | 0.71 | 0.36 | 129 | 94 |
| 34 | 0.71 | 0.43 | 116 | 94 |
| 35 | 0.71 | 0.50 | 106 | 72 |
| 36 | 0.83 | 0.25 | 114 | 98 |
| 37 | 0.83 | 0.33 | 130 | 107 |
| 38 | 0.83 | 0.41 | 121 | 102 |
| 39 | 0.83 | 0.50 | 116 | 97 |

Examples 40-51

Coating solutions weighing a total of 5 grams were prepared by dissolving 0.71 grams IEM-AGM (Lot C) and a co-monomer in the amounts listed in Table 6, and 0.0071 gram MBA in 50/50 deionized water/isopropanol by volume, and adding 62.5 μL of the photoinitiator solution in Example 14. The co-monomers were PEG200MA (polyethyleneglycol 200 monomethacrylate; Polysciences, Inc.), and SR 550 (polyethyleneglycol monomethylether monomethacrylate; Sartomer). Primed membranes were coated, grafted, washed, dried, and tested as in Example 1. Results are listed in Table 6.

TABLE 6

| | | Comonomer | BSA Capacity (mg/mL) | |
|---|---|---|---|---|
| Example | Comonomer | (grams) | Static | Dynamic |
| 40 | PEG200MA | 0.07 | 132 | 87 |
| 41 | PEG200MA | 0.14 | 136 | 99 |
| 42 | PEG200MA | 0.21 | 140 | 95 |
| 43 | PEG200MA | 0.29 | 144 | 98 |
| 44 | PEG200MA | 0.36 | 144 | 96 |
| 45 | PEG200MA | 0.43 | 140 | 100 |
| 46 | SR 550 | 0.14 | 126 | 65 |
| 47 | SR 550 | 0.21 | 132 | 55 |
| 48 | SR 550 | 0.29 | 126 | 77 |
| 49 | SR 550 | 0.36 | 132 | 68 |
| 50 | SR 550 | 0.43 | 127 | 73 |
| 51 | SR 550 | 0.50 | 125 | 73 |

Examples 52-60

Preparation of 4-(2-(acryloylamino)-2-methylpropionylamino)butyl guanidinium triethylammonium sulfate (VDM-AGM triethylammonium sulfate)

Solid: A solution of agmatine sulfate (21.4 g, 94 mmol) dissolved in 100 mL of deionized water was added to a stirred solution of triethylamine (13.9 mL, 100 mmol) in ethanol. The cloudy solution was treated with additional water (10 mL) and became homogenous. The reaction mixture was placed in a water bath and 4,4-dimethyl-2-vinyl-1,3-oxazol-5(4H)-one (14.0 g, 101 mmol) was added dropwise over a five minute period. After stirring overnight the reaction mixture was concentrated under vacuum at ambient temperature until the volume was approximately 50 mL. The mixture was then lyophilized to form 36 grams of VDM-AGM white powder.

Solution: A solution of agmatine sulfate (16.95 g, 74.3 mmol) dissolved in 65 mL of deionized water was treated with triethylamine (7.50 g, 74.3 mmol). The reaction mixture was placed in a water bath and 4,4-dimethyl-2-vinyl-1,3-oxazol-5(4H)-one (10.56 g, 75.9 mmol) was added dropwise over 10 minutes. The solution was allowed to stir for 90 min after which time NMR showed complete conversion to 4-(2-(acryloylamino)-2-methylpropionylamino)butyl guanidinium triethylammonium sulfate. $^1$H NMR (500 MHz, D$_2$O) δ 6.20 (m, 1H), 6.06 (m, 1H), 5.67 (d, 1H), 3.12-3.05 (m, 10H), 1.48-1.42 (m, 4H), 1.37 (s, 6H), 1.18 (t, J=7.3 Hz, 9 H).

Coating solutions weighing 5 grams total were prepared by dissolving solid VDM-AGM, a comonomer, and MBA in the amounts listed in Table 7 in deionized water and adding 31.2 μL of the photoinitiator solution of Example 14. Primed membranes were coated, grafted, washed, dried and tested as described in Example 1. Results are listed in Table 7. "Am" is acrylamide.

TABLE 7

| Ex | VDM-AGM (grams) | MBA (grams) | Comonomer | Comonomer (grams) | BSA Capacity (mg/mL) Static | BSA Capacity (mg/mL) Dynamic |
|---|---|---|---|---|---|---|
| 52 | 0.25 | 0.0025 | None | 0 | 21 | NM |
| 53 | 0.5 | 0.005 | None | 0 | 102 | 45 |
| 54 | 1.0 | 0.01 | None | 0 | 152 | 1 |
| 55 | 0.625 | 0.0062 | AMPS-Na | 0.0312 | 120 | 55 |
| 56 | 0.625 | 0.0062 | AMPS-Na | 0.0625 | 96 | 46 |
| 57 | 0.5938 | 0.0062 | DMA | 0.0312 | 155 | 0 |
| 58 | 0.5938 | 0.0062 | Am | 0.0312 | 171 | 0 |
| 59 | 0.5625 | 0.0062 | DMA | 0.0625 | 181 | 0 |
| 60 | 0.5625 | 0.0062 | Am | 0.0625 | 192 | 0 |

The following Examples illustrate priming conditions for preparing a nylon membrane suitable as a substrate for grafting.

Example 61

A priming solution was prepared by mixing 6.67 grams of PEI (Polyethylenimine; Polysciences, Inc.) with 6.67 grams of IPA to form a 15% by weight solution. Vinyldimethylazlactone (VDM, 0.64 grams, enough to react with 10% of the amine groups of the PEI) was added and mixed on a rocker. Within 15 minutes, the mixture had gelled, presumably indicating that crosslinking occurred via Michael addition of amine groups to the double bond of the acrylamide derived from VDM.

Example 62

A priming solution for a nylon membrane was prepared according to the procedure of Example 61 except that the PEI solution was diluted to a total of 40 grams with isopropanol (5% solids) before addition of the VDM. The reaction mixture was still fluid after 5 hours, but had gelled after overnight reaction.

Example 63

A priming solution for a nylon membrane was prepared according to the procedure of Example 62 except that 0.66 grams of GMA (Glycidyl methacrylate) was used instead of VDM. The reaction mixture was still fluid after 18 hours reaction time.

Examples 64-67

For Example 64, a 1% solids by weight solution was prepared from by mixing 1.67 g PEI (30% solids by weight in aqueous solution) with IPA to 50 grams total. A second 50 gram solution was prepared by dissolving 14.7 mg butanediol diglycidylether (BUDGE), which was sufficient to react with 2.5% of the amine groups of the PEI, in IPA solution. The two solutions were mixed briefly to provide a 0.5% solids priming solution. Squares (10 cm) of a nylon 66 membrane (#080ZN; 3M Purification, Inc.) were dip coated with the priming solution and excess solution was removed using a #14 wire-wound coating rod. The coated membranes were allowed to air dry at ambient temperature for at least 15 minutes. Some of the membranes were dip-coated a second time and allowed to air dry. Following drying, samples of each coated membrane were weighed to determine the coating weight, and placed in 250 mL polyethylene bottles filled with deionized water. The bottles were sealed, and agitated overnight to extract any unbound material. After drying, the membranes were weighed to determine the amount of coating removed. Washed and unwashed membranes were tested for BSA capacity to determine the effectiveness of the crosslinking (Table 8).

Examples 65, 66, and 67 were prepared in the same manner except that the priming solutions had 5%, 10%, and 20% BUDGE, respectively (Table 8).

TABLE 8

| Ex | % Crosslinker | Number of Coats | Static BSA Capacity (mg/mL) Unwashed | Static BSA Capacity (mg/mL) Washed | % Coating Removed |
|---|---|---|---|---|---|
| 64 | 2.5 | 1 | 20 | 15 | 28 |
| 64 | 2.5 | 2 | 54 | 20 | 63 |
| 65 | 5 | 1 | 21 | 17 | 18 |
| 65 | 5 | 2 | 55 | 26 | 54 |
| 66 | 10 | 1 | 23 | 19 | 16 |
| 66 | 10 | 2 | 57 | 35 | 39 |
| 67 | 20 | 1 | 28 | 27 | 5 |
| 67 | 20 | 2 | 55 | 46 | 17 |

Examples 68-71

PEI Priming solutions were prepared at a final concentration of 1% solids with the amounts of crosslinker in Table 9, and membranes were coated as described in Example 64. Some samples were air-dried as in Example 4, and others were dried in an oven at 45-50° C. for 2 hours. All of the samples were washed with deionized water as in Example 64, and measured for static BSA capacity (Table 9).

TABLE 9

| Example | % Crosslinker | Static BSA Capacity (mg/mL) Air-dried | Static BSA Capacity (mg/mL) Oven dried |
|---|---|---|---|
| 68 | 2.5 | 16 | 29 |
| 69 | 5 | 21 | 22 |
| 70 | 10 | 24 | 14 |
| 71 | 20 | 28 | 10 |

Examples 72-75

A primed nylon membrane for Example 72 was prepared according to the procedure described for "Preparation of primed nylon membrane". Example 73-75 were prepared in the same manner with the following exceptions: Example 73 had no GMA; Example 74 was prepared with VDM as a graft site monomer instead of GMA; and Example 75 was prepared with deionized water as the solvent for primer solution. For each example, an additional primed membrane was washed with acetate buffer (50 mM sodium acetate, 40 mM sodium chloride, pH 4.5) for 1 hour, followed by a deionized water wash for 1 hour, and then allowed to air-dry. All of the membranes were grafted according as described in Example 32, except that the coating solvent was methanol, and tested for static and dynamic BSA capacities (Table 10).

TABLE 10

| Ex | Wash | Static BSA Capacity (mg/mL) Primed Only | Static BSA Capacity (mg/mL) Grafted | Dynamic BSA Capacity (mg/mL) |
|---|---|---|---|---|
| 72 | No | 59 | 126 | 97 |
|  | Yes | 25 | 127 | 92 |
| 73 | No | 62 | 115 | 64 |
|  | Yes | 22 | 126 | 33 |
| 74 | No | 18 | 90 | 70 |
|  | Yes | 20 | 93 | 71 |
| 75 | No | 19 | 104 | 82 |
|  | Yes | 19 | 105 | 83 |

Examples 76-79

In Examples 76-79 nylon membranes were prepared and grafted according to the procedure described in Example 72 except that the weight percent (based on the weight of the IEM-AGM monomer) of MBA in the coating solution was varied (Table 11).

Examples 80-84 were prepared in the same manner except that unprimed nylon membranes (#080ZN; 3M Purification, Inc.) were grafted and tested (Table 11).

TABLE 11

| Example | % MBA | BSA Capacity (mg/mL) Static | BSA Capacity (mg/mL) Dynamic |
|---|---|---|---|
| 76 | 0.5 | 102 | 114 |
| 77 | 1 | 112 | 114 |
| 78 | 2 | 132 | 105 |
| 79 | 3 | 132 | 78 |
| 80 | 0.5 | 100 | 2 |
| 81 | 1 | 111 | 28 |
| 82 | 2 | 119 | 99 |
| 83 | 3 | 100 | 68 |
| 84 | 4 | 80 | 57 |

Examples 85-87

A coating solution was prepared from 17.0 grams of IEM-AGM (assayed to be 58.8% pure by NMR, 10.0 grams actual ligand monomer) and 0.5 grams VAZPIA (prepared as disclosed in Example 1 of U.S. Pat. No. 5,506,279), dissolved in 2 grams of methanol, and diluted to 50 grams total with deionized water. Portions of this solution were formulated for grafting by adding 0, 1, or 2% of MBA based on the weight of ligand monomer for Examples 85, 85, and 87, respectively. The nylon membranes were UV-grafted according to the procedure described in Example 1, using an irradiation time of 45 minutes per side, washed, dried, and analyzed for BSA capacities (Table 12).

TABLE 12

| Example | % MBA | BSA Capacity (mg/mL) Static | BSA Capacity (mg/mL) Dynamic |
|---|---|---|---|
| 85 | 0 | 93 | 49 |
| 86 | 1 | 95 | 73 |
| 87 | 2 | 92 | 88 |

Examples 88-93

Nylon membranes were prepared with the priming solution as described above in Example 72 except that 5% GMA based on amount of amine groups in the PEI was used for Example 88, 10% GMA for Example 89, and 15% GMA for Example 90. Similarly, membranes were primed using 5%, 10%, and 15% VDM to provide the graft sites, Examples 91-93, respectively. The membranes were all grafted with diacetone acrylamide and functionalized according to the procedure described in Example 3 and evaluated for static BSA capacity (Table 13).

TABLE 13

| Example | Graft Site Component Monomer | Graft Site Component Weight % | Static BSA Capacity (mg/mL) |
|---|---|---|---|
| 88 | GMA | 5 | 93 |
| 89 | GMA | 10 | 91 |
| 90 | GMA | 15 | 93 |
| 91 | VDM | 5 | 102 |
| 92 | VDM | 10 | 94 |
| 93 | VDM | 15 | 90 |

Examples 94-98

Coating solutions weighing a total of 5 grams each were prepared by dissolving IEM-AGM (nominally 96% pure by NMR) and PEG400MA in the amounts listed in Table 14, and 1% MBA by weight based on the amount of IEM-AGM, in methanol, and adding 31.2 μL of the photoinitiator solution of Example 14. Primed membranes were coated, grafted, washed and dried as described in Example 1. Following the measurement of dynamic binding capacity as described in the Test Methods section, any bound protein was eluted by washing with 1 M NaCl solution, re-equilibrated with 25 mM TRIS buffer containing 50 mM NaCl, pH 8. The dynamic capacity test was then repeated using a 1 mg/mL BSA solution in the same TRIS/salt buffer. Dynamic capacity results are listed in the Table as "Dynamic (salt)". These Examples illustrate that these highly charged membranes sometimes perform better in higher conductivity media.

TABLE 14

| Example | IEM-AGM (grams) | PEG400MA (grams) | BSA Capacity (mg/mL) Static | BSA Capacity (mg/mL) Dynamic | BSA Capacity (mg/mL) Dynamic (salt) |
|---|---|---|---|---|---|
| 94 | 0.60 | 0.24 | 119 | 82 | 90 |
| 95 | 0.65 | 0.26 | 121 | 23 | 100 |
| 96 | 0.70 | 0.28 | 120 | 8 | 111 |
| 97 | 0.75 | 0.30 | 117 | 11 | 108 |
| 98 | 0.80 | 0.32 | 106 | 2 | 117 |

Examples 99-101

Synthesis of 4-(2-(methacryloyloxy)ethylaminocarbonylamino)butyl guanidinium sodium sulfate (IEM-AGM sodium sulfate)

Agmatine sulfate (100 g, 397 mmol) was dissolved in 400 mL of aqueous 1.00 N NaOH. Acetone (200 mL) was then added and the stirred mixture was cooled to about 10° C. in a cold water bath. An additional 80 mL of $H_2O$ was added to keep the agmatine sulfate in solution. 2-isocyanatoethyl methacrylate (58.0 mL, 411 mmol) was then added to the reaction mixture, via an addition funnel, over a period of 30 min. After stirring an additional 45 min, the reaction mixture was placed on a rotary evaporator at ambient temperature. After pulling off most of the acetone, the reaction mixture was transferred to a separatory funnel and washed with ethyl acetate (2×250 mL) and methylene chloride (2×200 mL). The remaining aqueous solution was adjusted to pH 7 by addition of a small amount of dilute sulfuric acid and then placed on a rotary evaporator at ambient temperature to draw off any remaining volatiles. Lyophilization yielded the title compound (162 g) as a white powder. $^1$H NMR (500 MHz, D$_2$O) δ 6.14 (s, 1H), 5.73 (s, 1H), 4.23 (t, J=5.2 Hz, 2H), 3.45 (t, J=5.4 Hz, 2H), 3.18 (t, J=7.0 Hz, 2H), 3.12 (t, J=6.4 Hz, 2H), 1.22 (s, 3H), 1.61-1.48 (m, 4H).

Synthesis of 4-(2-(methacryloyloxy)ethylaminocarbonylamino)butyl guanidinium hemisulfate (IEM-AGM hemisulfate)

A solution of agmatine hemisulfate (2.00 g, 11.2 mmol) dissolved in 20 mL of ethanol was treated with 2-isocyanatoethyl methacrylate (1.50 mL, 10.6 mmol) over the course of a few minutes. The solution was allowed to stir for 30 min after which time the reaction mixture was concentrated at ambient temperature. The resulting syrup was concentrated twice with toluene to give the title compound as a white foam. $^1$H NMR (500 MHz, D$_2$O) δ 6.13 (s, 1H), 5.73 (s, 1H), 4.23 (t, J=4.8 Hz, 2H), 3.44 (t, J=4.8 Hz, 2H), 3.18 (t, J=7.0 Hz, 2H), 3.11 (t, J=6.7 Hz, 2H), 1.92 (s, 3H), 1.65-1.49 (m, 4H).

Coating solutions weighing a total of 5 grams each were prepared by dissolving IEM-AGM (counterion noted in Table 15) and PEG400MA in the amounts listed in Table 15, and 1% MBA by weight based on the amount of IEM-AGM, in methanol, and adding 31.2 µL of the photoinitiator solution of Example 14. Primed membranes were coated, grafted, washed and dried as described in Example 1. Dynamic capacities were measured using BSA dissolved in the TRIS/NaCl buffer described in Example 94.

TABLE 15

| Example | Counterion | IEM-AGM (grams) | PEG400MA (grams) | BSA Capacity (mg/mL) Static | BSA Capacity (mg/mL) Dynamic |
|---|---|---|---|---|---|
| 99 | sodium sulfate | 0.50 | 0.20 | 131 | 91 |
| 100 | sodium sulfate | 0.67 | 0.27 | 116 | 112 |
| 101 | hemisulfate | 0.55 | 0.22 | 130 | 106 |

Example 102

Synthesis of 6-(2-(acryloylamino)-2-methylpropionylamino)hexyl guanidinium sodium sulfate Aminohexylguanidine sulfate (32.4 g, 127 mmol) was dissolved in 120 mL of aqueous 1.00 N NaOH. Acetone (60 mL) was then added and the stirred mixture was cooled to about 10° C. in a cold water bath. An additional 60 mL of H$_2$O was added to keep the aminohexylguanidine sulfate in solution. 4,4-dimethyl-2-vinyl-1,3-oxazol-5(4H)-one (17.6 g, 137 mmol) was then added to the reaction mixture, via an addition funnel, over a period of 10 min. After stirring an additional 60 min, the reaction mixture was placed on a rotary evaporator at ambient temperature. After pulling off most of the acetone, the reaction mixture was transferred to a separatory funnel and washed with ethyl acetate (2×75 mL) and methylene chloride (2×25 mL). The remaining aqueous solution was brought to pH 7 by addition of dilute sulfuric acid and then placed on a rotary evaporator at ambient temperature to draw off any remaining volatiles. Lyophilization yielded the title compound (49 g) as a white powder $^1$H NMR (500 MHz, D$_2$O) δ 6.37 (m, 1H), 6.25 (m, 1H), 5.84 (m, 1H), 3.26-3.24 (m, 4H), 1.68-1.38 (m, 14H). This monomer (0.71 grams), MBA (0.07 grams), PEG400MA (0.28 grams), and photoinitiator (31.2 µL of the photoinitiator solution of Example 14) were dissolved in enough methanol to provide 5 grams of coating solution. Primed membranes were coated, grafted, washed and dried as described in Example 1. Static and dynamic capacities for the grafted membrane were 110 and 71 mg/mL, respectively.

Example 103

HCP and DNA removal—Salt Tolerance

Membranes prepared according to the recipe of Example 96 were analyzed for binding of HCP (host cell proteins) and DNA by passing diafiltered CHO cell culture solutions through a 6-layer stack of the membranes punched out into 25-mm diameter disks and placed in a 25 mm diameter holder attached to an AKTA chromatography system (GE Healthcare, NY). The challenge solution was prepared by first filtering CHO cell culture with a 0.2 um filter then concentrating and diafiltering the solution into 25 mM TRIS buffer, pH 8. The diafiltration was performed on a Millipore Labscale TFF System with a Pellicon Biomax 50 cassette using 8 volumes of TRIS. The resulting diafiltered material had a HCP concentration of 225000 ng/mL, DNA concentration of 75000 ng/mL and a conductivity of 1.5 mS/cm. To demonstrate salt tolerance, solutions of this material with higher salt concentrations were prepared by adding 5.0 M NaCl to reach conductivity levels of 5, 10, 20, 25, 30, and 40 mS/cm. The resulting challenge solutions were pumped through the membrane stack at a flow rate of 3 mL/min and the FT pool was collected with a fraction collector Frac-950 (GE Healthcare, NY). The HCP concentration of each pool was measured with a Chinese Hamster Ovary Host Cell Protein—3$^{rd}$ Generation ELISA kit (Cygnus Technologies, Inc) following the standard procedure. DNA concentrations were measure with a Quant-iT PicoGreen dsDNA Assay Kit (Invitrogen). Results are listed in Table 16 as log reduction values (LRV) relative to the starting solution.

TABLE 16

| Conductivity (mS/cm) | DNA (LRV) | HCP (LRV) |
|---|---|---|
| 1.5 | 2.2 | 1.7 |
| 5 | 2 | 2 |
| 10 | 2.5 | 1.7 |
| 20 | 3.1 | 1.7 |
| 25 | 2.9 | 1.2 |
| 30 | 2 | 0.9 |
| 40 | 1.9 | 0.8 |

Example 104

A coating solution was prepared from 10 grams of N-(3-dimethylaminopropyl)-acrylamide, 0.1 grams of MBA, 0.5 grams of Irgacure 2959, and 90 grams of deionized water. A primed membrane was coated and UV-grafted with this solution according to the procedure described in Example 1, washed, and dried. When assayed for static BSA capacity, this membrane absorbed all of the BSA from solution, indicating a BSA capacity of >195 mg/mL.

The invention claimed is:

1. A ligand functional substrate comprising:
   a) a substrate
   b) a primer layer disposed on the substrate comprising:
      a crosslinked polyamine polymer having ethylenically unsaturated polymerizable groups;
   c) a ligand-functional alkenyl (co)polymer layer grafted to the ethylenically unsaturated polymerizable group of the primer layer.

2. The ligand-functional substrate of claim 1, wherein the crosslinked polyamine polymer having ethylenically unsaturated polymerizable groups is the reaction product of:
   1) a polyamine polymer
   2) a polyfunctional crosslinking agent for the polyamine polymer; and
   3) a monomer having an amine-reactive functional group and an ethylenically unsaturated polymerizable group.

3. The ligand-functional substrate of claim 1, wherein said ligand is selected from the group consisting of tyrosinol, tryptophanol, octopamine, 2-aminobenzimidazole, 1,3-diamino-2-hydroxypropane, tris(2-aminoethyl)amine, diethylenetriamine, triethylenetetramine, tetraethylenepentamine, agmatine, guanidine and biguanide ligands.

4. The ligand-functional substrate of claim 1, wherein the ligand-functional alkenyl (co)polymer comprises polymerized monomer units of the formula:

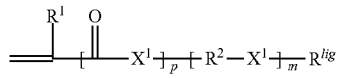

wherein
$R^1$ is H or $C_1$-$C_4$ alkyl;
$R^2$ is a (hetero)hydrocarbyl group;
$X^1$ is —O— or —$NR^3$—, where $R^3$ is independently H or $C_1$-$C_4$ alkyl;
$R^{lig}$ is a ligand-containing group,
p is 0 or 1; and
m is 0 or 1.

5. The ligand-functional substrate of claim 1, wherein the ligand-functional alkenyl (co)polymer comprises polymerized monomer units of the formula:

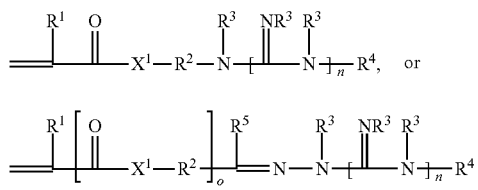

wherein
$R^1$ is H or $C_1$-$C_4$ alkyl;
$R^2$ is a (hetero)hydrocarbyl group;
each $R^3$ is independently H or hydrocarbyl;
$R^4$ is H, $C_1$-C4 alkyl or —$N(R^3)2$;
$R^5$ is H or hydrocarbyl;
$X^1$ is —O— or —$NR^3$—,
o is 0 or 1, and
n is 1 or 2.

6. The ligand-functional substrate of claim 1, wherein the ligand-functional alkenyl (co)polymer further comprises polymerized polar monomer units.

7. The ligand-functional substrate of claim 6, wherein the ligand-functional alkenyl (co)polymer further comprises polymerized cationic or anionic monomer units.

8. The ligand-functional substrate of claim 6, wherein the polar monomer units comprise the poly(oxyalkylene) (meth)acrylate monomer units.

9. The ligand-functional substrate of claim 8, wherein the poly(oxyalkylene) (meth)acrylate monomer units are of the formula: $CH_2$=$CR^1$—C(O)—$X^1$—(CH($R^1$)—CH2—O)$_n$—$R^1$, wherein each $R^1$ is independently H or $C_1$-$C_4$ alkyl, $X^1$ is —O— or —$NR^3$—, where $R^3$ is H or $C_1$-$C_4$ alkyl and n is 2 to 100.

10. The ligand-functional substrate of claim 2 wherein the polyamine polymer is selected from the group consisting of polyethylenimine, polylysine, polyaminoamides, polydimethylamine-epichlorohydrin-ethylenediamine, polyaminosiloxanes and dendrimers formed from polyamidoamine and polypropylenimine.

11. The ligand-functional substrate of claim 1 wherein said primer layer comprises 0.1 to 5 wt. % of the substrate.

12. The ligand-functional substrate of claim 1 wherein said ligand-functional alkenyl (co)polymer comprises 5 to 30 wt.% of the ligand functional substrate.

13. The ligand-functional substrate of claim 1 wherein said ligand groups are of the formula:

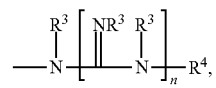

wherein
each $R^3$ is independently H or $C_1$-$C_4$ alkyl;
$R^4$ is H, $C_1$-$C_4$ alkyl or —$N(R^3)_2$; and
n is 1 or 2.

14. The ligand-functionalized substrate of claim 1 comprising a ligand-functional alkenyl (co)polymer layer of the formula:

$-(M^{Lig})_y-(M^{Hydrophil})_x-(M^{crosslink})_z-$, wherein
$(M^{Hydrophil})_x$ are hydrophilic monomer units having "x" polymerized monomer units,
$(M^{Lig})_y$ are ligand functional monomer units having "y" polymerized monomer units,
$(M^{crosslink})$ are multifunctional (meth)acryloyl monomer units having "z" polymerized monomer units,
y is 10 to 100 wt. % of the monomer units;
x is 0 to 90 wt. % of the monomer units and;
z is 0 to 5 wt. % of the monomer units, based on 100 wt. % total monomers.

15. The ligand-functionalized substrate of claim 2 wherein the polyfunctional crosslinking agent is of the formula:

$R^8$—(Z)$_y$, where $R^8$ is a (hetero)hydrocarbyl group, Z is an amine-reactive group, and y is ≥2.

16. The ligand-functionalized substrate of claim 2 wherein said polyfunctional crosslinking agent of the formula:

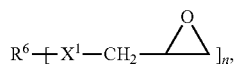

where
- $R^6$ is an alkylene or arylene having a valence of n;
- $X^1$ is —O— or —NR$^1$13, where $R^1$ is H or $C_1$-$C_4$ alkyl,
- and n is 2 to 6.

17. The ligand-functionalized substrate of claim 2 wherein said monomer having an amine-reactive functional group is of the formula:

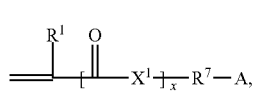     III wherein
- $X^1$ is —O— or —NR$^1$—, where $R^1$ is H or $C_1$-$C_4$ alkyl,
- $R^1$ is H or $C_1$-$C_4$ alkyl;
- $R^7$ is a single bond or a hydrocarbyl linking group,
- A is a functional group that is reactive with the amino groups of the polyamine polymer, and
- x is 0 or 1.

18. The ligand-functionalized substrate of claim 15 wherein the crosslinking agent for the polyamine polymer is used in amounts wherein the number of equivalents of amine reactive groups Z is at least 2% to 20%, relative to the equivalent of amine groups in the polyamine polymer.

* * * * *

UNITED STATES PATENT AND TRADEMARK OFFICE
CERTIFICATE OF CORRECTION

PATENT NO. : 9,272,246 B2
APPLICATION NO. : 13/353413
DATED : March 1, 2016
INVENTOR(S) : Jerald Rasmussen Page 1 of 1

It is certified that error appears in the above-identified patent and that said Letters Patent is hereby corrected as shown below:

Specification

Column 10,
Line 47, delete "—NR—," and insert -- —NR$^3$—, -- , therefor.

Claims

Column 33,
Line 63, in Claim 5, delete "C$_1$-C4" and insert -- C$_1$-C$_4$ --, therefor.

Column 34,
Line 52, in Claim 14, delete "(M$^{crosslink}$)are" and insert -- (M$^{crosslink}$) are --, therefor.

Column 35,
Line 8, in Claim 16, delete "—NR$^1$13 ," and insert -- —NR$^1$1, --, therefor.

Column 35,
Line 15, in Claim 17, after " 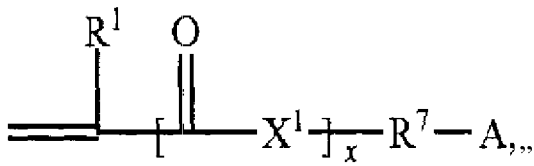 delete "III".

Signed and Sealed this
Nineteenth Day of July, 2016

Michelle K. Lee
*Director of the United States Patent and Trademark Office*